(12) United States Patent
Lee et al.

(10) Patent No.: US 12,333,724 B2
(45) Date of Patent: Jun. 17, 2025

(54) ELECTRONIC DEVICE FOR ANALYZING ENDOSCOPIC IMAGES AND PROVIDING INFORMATION ABOUT A PLURALITY OF LESIONS, AND ENDOSCOPIC EXAMINATION SYSTEM INCLUDING THE ELECTRONIC DEVICE

(71) Applicant: PREVENOTICS Inc., Seoul (KR)

(72) Inventors: Junwoo Lee, Anyang-si (KR); Soo Youn Chang, Seoul (KR)

(73) Assignee: PREVENOTICS Inc., Seoul (KR)

( * ) Notice: Subject to any disclaimer, the term of this patent is extended or adjusted under 35 U.S.C. 154(b) by 0 days.

(21) Appl. No.: 18/919,504

(22) Filed: Oct. 18, 2024

(65) Prior Publication Data

US 2025/0045921 A1    Feb. 6, 2025

Related U.S. Application Data

(63) Continuation of application No. PCT/KR2023/019632, filed on Dec. 1, 2023.

(30) Foreign Application Priority Data

| Dec. 1, 2022 | (KR) | .................. 10-2022-0165705 |
| Jan. 30, 2023 | (KR) | .................. 10-2023-0011468 |

(Continued)

(51) Int. Cl.
  *G06T 7/00*        (2017.01)
(52) U.S. Cl.
  CPC .. *G06T 7/0012* (2013.01); *G06T 2207/10068* (2013.01); *G06T 2207/30096* (2013.01)

(58) Field of Classification Search
  CPC ............ A61B 1/0005; A61B 1/000096; A61B 1/00009; A61B 1/2736; A61B 1/00;
  (Continued)

(56) References Cited

U.S. PATENT DOCUMENTS

| 8,939,892 B2 * | 1/2015 | Miyamoto | ................ G06T 7/74 |
| | | | 600/117 |
| 2004/0102693 A1 | 5/2004 | Jenkins | |

(Continued)

FOREIGN PATENT DOCUMENTS

| KR | 10-2021-0134121 A | 11/2021 |
| KR | 10-2022-0121956 A | 9/2022 |

(Continued)

OTHER PUBLICATIONS

International Search Report for PCT/KR2023/019632, dated Mar. 6, 2024.

(Continued)

*Primary Examiner* — Aaron W Carter
*Assistant Examiner* — Courtney Joan Nelson
(74) *Attorney, Agent, or Firm* — NKL Law; Jae Youn Kim

(57) ABSTRACT

According to one embodiment of the present disclosure, an electronic device for processing an endoscopic image may comprise a memory configured to store instructions and at least one processor electronically connected to the memory and configured to execute at least a portion of the instructions, wherein the at least one processor obtains an indicator associated with at least one lesion by operating in at least one of a plurality of operation modes.

15 Claims, 34 Drawing Sheets

(30) Foreign Application Priority Data

Jan. 30, 2023 (KR) .......................... 10-2023-0011469
Jan. 30, 2023 (KR) .......................... 10-2023-0011470

(58) Field of Classification Search
CPC .................. A61B 1/041; A61B 5/7425; G06T 2207/10068; G06T 7/0012; G06T 2207/30028; G06T 2207/30096; G06T 7/00; G06T 2210/41; G06T 2207/30092; G06T 2207/30004; G06T 2207/30032; G16H 50/20; G16H 30/00; G16H 30/40; G06V 10/761; G06V 2201/03; G06N 3/045

See application file for complete search history.

(56) References Cited

U.S. PATENT DOCUMENTS

2020/0242764 A1* 7/2020 Aoyama ............... A61B 5/7275
2020/0337537 A1* 10/2020 Hirasawa .......... A61B 1/000096
2022/0020496 A1* 1/2022 Saito ..................... G06T 7/0012

FOREIGN PATENT DOCUMENTS

KR      10-2022-0122312 A      9/2022
KR         10-2572544 B1       8/2023

OTHER PUBLICATIONS

Office Action of KIPO for Korean application No. 10-2023-0011468, issued on Aug. 23, 2023.
Written Opinion for PCT/KR2023/019632, dated Mar. 6, 2024.

* cited by examiner

FIG. 31

```
3100 ─ EXAMINATION REPORT

3110 ─ ( PATIENT INFORMATION )

NAME                EXAMINING SITE
        DATE OF BIRTH       EXAMINING DOCTOR
        SEX                 EXAMINING DATE

3120 ─ ( Picrtures )

[ ][ ][ ][ ][ ]

3130 ─ ( Dotor's Comments )

■ OOOYOU HAVE NOTABLE INTESTINAL METAPLASIA IN THE GASTRIC BODY
        □ TYPICALLY EXPECTED TO BE EVERY THREE MONTHS
        □ COMPARED TO THE 14 OCTOBER 2023 SCAN,
        □ THE RANGE OF INTESTINAL METAPLASIA IN THE
          GASTRIC BODY HAS INCREASED BY APPROXIMATELY 3%

3140 ─ ( DISEASE GUIDANCE )

■ Atrophic Gastritis   ■ Intestinal Metaplasia   □ Gastric adenoma   □ Gastric Cancer

3150 ─ ( PATIENT SELF-PREVENTION MANAGEMENT PLATFORM )

HELP PATIENTS MANAGE THEIR GASTRIC CANCER
        PREVENTION THROUGH A PREVENTIVE CARE PLATFORM      [QR]
```

ELECTRONIC DEVICE FOR ANALYZING ENDOSCOPIC IMAGES AND PROVIDING INFORMATION ABOUT A PLURALITY OF LESIONS, AND ENDOSCOPIC EXAMINATION SYSTEM INCLUDING THE ELECTRONIC DEVICE

CROSS-REFERENCE TO RELATED APPLICATIONS

This application is a bypass continuation of International Application No. PCT/KR2023/019632, filed on Dec. 1, 2023, which is based on and claims priority to Korean Patent Application No. 10-2022-0165705, filed on Dec. 1, 2022, Korean Patent Application No. 10-2023-0011468, filed on Jan. 30, 2023, Korean Patent Application No. 10-2023-0011469, filed on Jan. 30, 2023, and Korean Patent Application No. 10-2023-0011470, filed on Jan. 30, 2023, in the Korean Intellectual Property Office, the disclosures of which are incorporated by reference herein in their entireties.

TECHNICAL FIELD

The present disclosure relates to an electronic device and method for diagnosing lesions by analyzing medical images.

BACKGROUND ART

Gastric cancer is a leading cause of cancer-related mortality, ranking fourth globally in cancer deaths. However, the prevalence and prevention strategies for gastric cancer vary by region and country. Notably, South Korea, along with Germany and Japan, has developed one of the most advanced endoscopic screening systems for gastric cancer prevention.

Despite these advancements, the practical execution of endoscopic screenings is often constrained by time limitations due to the scarcity of examination infrastructure and qualified personnel to manage the large volume of patients.

These constraints have driven research into methods for rapidly and accurately identifying areas of the gastric mucosa that may be cancerous by using artificial intelligence (AI) model to analyze endoscopic images.

However, due to the inherent complexity of integrating technology with medical diagnostic procedures, there are still challenges in efficiently utilizing limited medical resources. Presently, there is no standardized diagnostic system for detecting precancerous gastric conditions, such as intestinal metaplasia, which is a precursor to gastric cancer. Research indicates that the progression rate of gastric cancer in patients with intestinal metaplasia is approximately 12.4 cases per 10,000 patients. Identifying these precancerous conditions is extremely challenging because, unlike overt cancer, there are no clear boundaries separating the affected tissue from the surrounding mucosa. To accurately detect these precancerous conditions, it is crucial to develop techniques that can analyze images from multiple specific positions (landmarks) inside the body. Such techniques would enhance the accuracy of computational algorithms in identifying precancerous conditions that are otherwise difficult to discern visually.

Specifically, there is a pressing need for improved methods for capturing high-quality images of medically significant landmarks across the esophagus, stomach, and duodenum, and for comprehensive image analysis to predict the gastric cancer.

Additionally, as endoscopic image analysis evolves to provide diagnostic information for various types of lesions, it is expected that a user-friendly interface will become essential to effectively provide and communicate this information to users.

SUMMARY

Technical Problem

One aspect of the present disclosure is to provide a method and a device for processing endoscopic images to deliver information about various types of lesions.

Another aspect of the present disclosure is to effectively provide the information obtained from the processed endoscopic images to the user through a user-friendly interface.

The technical solutions presented in this disclosure are not limited to the aforementioned aspects. Additional solutions may be clear to those skilled in the art with reference to the following detailed description and the accompanying drawings.

Technical Solution

According to one embodiment of the present disclosure, an electronic device for processing endoscopic images may comprise: a memory configured to store instructions; and at least one processor electronically connected to the memory and configured to execute the instructions. The at least one processor obtains an indicator associated with at least one lesion by operating in at least one of a plurality of operating modes. The at least one processor obtains a plurality of image frames in the endoscopic image; obtains, in a first mode of operation, first detection information about a first type of lesion based on at least one of the plurality of image frames; and obtains, in a second mode of operation, second detection information about a second type of lesion based on at least two image frames respectively corresponding to predetermined at least two reference positions inside the body among the plurality of image frames.

In another embodiment, an operating method of an electronic device for processing endoscopic images may comprise: obtaining a plurality of image frames included in an endoscopic image by at least one processor in the electronic device; obtaining, according to a first mode of operation, first detection information about a first type of lesion based on at least one of the plurality of image frames; and obtaining, according to a second mode of operation, second detection information about a second type of lesion based on at least two image frames respectively corresponding to predetermined at least two reference positions inside the body among the plurality of image frames.

According to another embodiment, an endoscopic examination system may comprise: an endoscopic device for capturing an endoscopic image; and at least one processor. The at least one processor obtains, according to a first mode of operation, a plurality of image frames included in the endoscopic image, obtains first detection information about a first type of lesion based on at least one of the plurality of image frames, and obtains, according to a second mode of operation, second detection information about a second type of lesion based on at least two image frames respectively corresponding to predetermined at least two reference positions inside the body among the plurality of image frames.

According to another embodiment, an electronic device for providing information about a landmark image may comprise: a memory configured to store instructions; and at least one processor electronically connected to the memory and configured to execute the instructions. The at least one processor may play back the endoscopic image in a first area of a display and identify an image frame corresponding to a plurality of predetermined landmarks based on the endoscopic image. The landmarks are defined as an anatomical reference position inside the body for lesion detection. The processor may also display at least one visual display in a second area of the display based on whether the image frame corresponding to the plurality of predetermined landmarks is obtained. The second area includes a plurality of subareas corresponding to each of the predetermined landmarks.

According to another embodiment of the present disclosure, an operating method of an electronic device for processing an endoscopic image may comprise: playing back the endoscopic image in a first area of a display by at least one processor in the electronic device; identifying an image frame corresponding to a plurality of landmarks predetermined based on the endoscopic image, the landmark being defined as an anatomical reference position inside a body for lesion detection; and displaying at least one visual display in a second area of the display based on whether an image frame corresponding to the predetermined plurality of landmarks is obtained, the second area including a plurality of subareas corresponding to each of the predetermined landmarks.

According to an embodiment of the present disclosure, an endoscopic examination system may comprise: a display; an endoscopic device for capturing an endoscopic image; and at least one processor. The at least one processor is configured to play back the endoscopic image in a first area of the display, identify an image frame corresponding to a plurality of predetermined landmarks based on the endoscopic image, the landmark being defined as an anatomical reference position inside a body for lesion detection. The processor may also display at least one visual display in a second area of the display based on whether an image frame corresponding to the predetermined plurality of landmarks is obtained, the second area including a plurality of subareas corresponding to each of the plurality of landmarks.

According to an embodiment of the present disclosure, an electronic device for providing information about a lesion may comprise: a memory configured to store instructions; and at least one processor electronically connected to the memory and configured to execute the instructions. The at least one processor may analyze a plurality of image frames included in an endoscopic image to provide information about a specific lesion. The processor may identify a first image frame corresponding to a first reference position and a second image frame corresponding to a second reference position based on the endoscopic image; obtain first lesion information indicating the degree of occurrence of a specific lesion at the first reference position based on the first image frame, obtain second lesion information indicating the degree of occurrence of a specific lesion at the second reference position based on the second image frame; and provide comprehensive information about a specific lesion based on the first lesion information and the second lesion information.

According to an embodiment of the present disclosure, an operating method of an electronic device for providing information about a lesion may comprise: identifying a first image frame corresponding to a first reference position and a second image frame corresponding to a second reference position based on the endoscopic image by at least one processor included in the electronic device; obtaining first lesion information indicating the degree of occurrence of a specific lesion at the first reference position based on the first image frame and obtaining second lesion information indicating the degree of occurrence of a specific lesion at the second reference position based on the second image frame; and providing comprehensive information about a specific lesion based on the first lesion information and the second lesion information.

According to an embodiment of the present disclosure, an endoscopic examination system may comprise: a display; an endoscopic device for obtaining an endoscopic image; and at least one processor. The at least one processor may identify a first image frame corresponding to a first reference position and a second image frame corresponding to a second reference position based on the endoscopic image; obtain first lesion information indicating a degree of occurrence of a specific lesion at the first reference position based on the first image frame; obtain second lesion information indicating a degree of occurrence of a specific lesion at the second reference position based on the second image frame; and provide comprehensive information about the specific lesion based on the first lesion information and the second lesion information using the display.

According to various embodiments, the technical solutions and their effects thereof are not limited to those mentioned solutions above. The solutions and effects that are not mentioned may be clear to those skilled in the art with reference to the following detailed description and the accompanying drawings.

Advantageous Effects

According to various embodiments, endoscopic images may be processed to provide information about different types of lesions.

Further, according to various embodiments, the information obtained by processing endoscopic images may be effectively presented to a user.

The effects of the embodiments included in this disclosure are not limited to those described above, and those not described will be apparent to one having ordinary skill in the art from this description and the accompanying drawings.

BRIEF DESCRIPTION OF DRAWINGS

FIG. 31 is a diagram illustrating a user interface for providing a result report of an endoscopic examination result by an electronic device according to various embodiments.

DETAILED DESCRIPTION OF EXEMPLARY EMBODIMENTS

Figure 1:
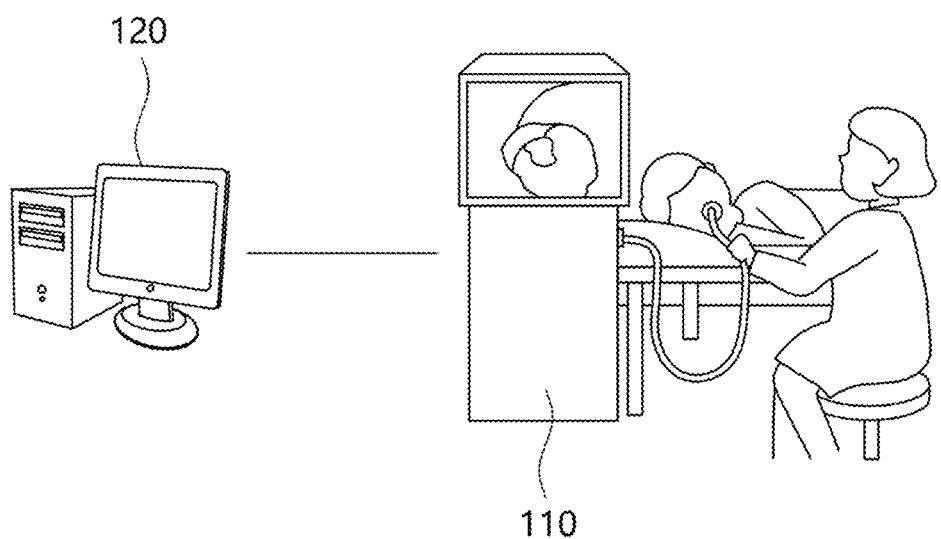
FIG. 1 is a diagram illustrating an embodiment of an endoscopic examination system 100 according to various embodiments.

Hereinafter, the embodiments of the present disclosure will be described in detail with reference to the accompanying drawings. In describing the embodiments, technical details that are well-known to those skilled in the art and are not directly related to the present disclosure will be omitted. This is to clearly describe the subject matter of the present disclosure by omitting redundant descriptions.

The embodiments presented in this specification are intended to clearly describe the spirit of the present invention to those of ordinary skill in the relevant art. The present invention is not limited to the embodiments described herein, and the scope of the present invention should be interpreted to encompass modifications or variations that do not depart from its spirit of the present invention.

Although the terminology used in this specification includes as general terms currently widely accepted for describing the functions in the present invention, interpretations of these terms may vary depending on the intentions of practitioners in the relevant field, precedents, or emerging technologies. In a case where a specific term is defined and used with different meanings, the specific meaning will be explicitly provided. Therefore, the terms used herein should be interpreted based on the substantive meaning and the overall context of this specification rather than their mere literal meaning.

The accompanying drawings are intended to easily describe the present invention, and the shapes depicted in the drawings may be exaggerated as necessary to aid understanding of the present invention. Thus, the scope of the present invention is not limited by the depictions in the drawings.

In this specification, each of the phrases such as "A or B," "at least one of A and B," "at least one of A or B," "A, B, or C," "at least one of A, B, and C," and "at least one of A, B, or C" may include any of the items enumerated in the corresponding phrase or all possible combinations thereof.

In cases where describing detailed configurations or functions known in relation to the present invention may make the subject matter ambiguous, such description will be omitted as necessary. Additionally, numerical designations (e.g., first, second) used in the description are merely symbols for differentiating one component from another component and do not imply a sequential or hierarchical order unless the context clearly indicates otherwise.

The suffixes "part," "module," and "unit" used for the components in this specification are provided for ease of writing and do not imply distinctive meaning, functions, or roles by themselves.

In other words, the embodiments of the disclosure are provided to make the disclosure complete and to give one of ordinary skill in the art to which the disclosure belongs a sense of the scope of the disclosure, and the invention of the disclosure is defined only by the scope of the claims. Throughout the specification, like reference numerals refer to like components.

The terms "first" and "second" may be used to describe various components, but these terms are only for differentiation purposes. The above terms are used only for the purpose of distinguishing one component from another, e.g. a first component may be named as a second component, and similarly a second component may be named as a first component, without departing from the scope of the rights according to the concepts of the present disclosure.

It should be understood that when an element is described as being "connected" or "coupled" to another element, there may be intervening elements in between or it may be directly connected or coupled to the other element. On the other hand, when an element is described as being "directly connected" or "directly coupled" to another element, it should be understood that there are no intervening elements. Other expressions that describe the relationship between elements (i.e., "between" and "immediately between", "neighboring to" and "directly neighboring to", or "adjacent to" and "directly adjacent to") should be interpreted similarly.

In the drawings, each block of the flowcharts and combinations of the flowcharts may be performed by computer program instructions. Since these computer program instructions may be incorporated into a processor of a general-purpose computer, special purpose computer, or other programmable data processing apparatus, the instructions executed by the processor of the computer or other programmable data processing apparatus create means for performing the functions described in the flowchart block(s). Since these computer program instructions may be stored in a computer-usable or computer-readable memory that can direct a computer or other programmable data processing apparatus to implement a function in a particular manner, the instructions stored in the computer-usable or computer-readable memory can produce articles of manufacture that include instructions for means to perform the functions described in the flowchart block(s). Since the computer program instructions may be mounted on a computer or other programmable data processing apparatus, a series of operational steps may be performed on the computer or other programmable data processing apparatus to produce a computer-executed process, and the instructions for the computer or other programmable data processing apparatus may provide steps for performing the functions described in the flowchart block(s).

A machine-readable storage medium may also be provided in the form of a non-transitory storage medium. Here, "non-transitory" means that the storage medium is a tangible device and does not contain a signal (e.g. electromagnetic wave), and this term does not distinguish between a case where data is semi-permanently stored in the storage medium and a case where data is temporarily stored.

Each block may represent a module, segment, or portion of code including one or more executable instructions designed to perform a specified logical function. It should be noted that in some embodiments, the functions mentioned in the blocks may occur in a different order than described. For example, two blocks shown in succession may be performed concurrently, simultaneously or in reverse order, depending on the functions they represent. For example, operations performed by a module, program, or other component may be executed sequentially, in parallel, repeatedly, or heuristically; one or more of the operations may be executed in a different order, omitted, or one or more other operations may be added.

The term "unit" used in this specification refers to software or hardware components such as Field Programmable Gate Array (FPGA) or Application Specific Integrated Circuit (ASIC). The "unit" performs specific roles but is not limited to software or hardware. The "unit" may be configured to reside in an addressable storage medium or to reproduce one or more processors. Accordingly, in some embodiments, the "unit" includes components such as software components, object-oriented software components, class components, processes, functions, attributes, procedures, subroutines, segments of program code, drivers, firmware, microcode, circuits, data, databases, data structures, tables, arrays, and variables. The functions provided in the components and "units" may be combined into fewer components and "units," or it may be disseminated into additional components and "units." These components and "units" may be implemented to reproduce one or more CPUs within a device or a secure multimedia card. Additionally, according to various embodiments of the present disclosure, the "units" may include one or more processors.

Hereinafter, the operating principles of the present disclosure will be described in detail with reference to the accompanying drawings. When describing the present disclosure, detailed descriptions of related known functions or configurations will be omitted if their inclusion may obscure the subject matter. The terms described below are defined considering the functions of the present disclosure and may vary depending on the user, operator, or customary practices. Therefore, definitions should be given consistent with the description throughout this specification.

According to an embodiment of the present disclosure, an electronic device for processing an endoscopic image may comprise: a memory configured to store instructions; and at least one processor electronically connected to the memory and configured to execute the instructions. The at least one processor may obtain an indicator associated with at least one lesion by operating in at least one of a plurality of operation modes. In a first mode of operation, the at least one processor may obtain first detection information for a first type of lesion based on at least one of the plurality of image frames. In a second mode of operation, the processor may obtain second detection information for a second type of lesion based on at least two image frames corresponding to respective predetermined at least two reference positions inside the body.

The first detection information may include a first indicator representing the probability that the identified area corresponds to a first type of lesion. The at least one processor may obtain the first indicator based on the at least one suspicious lesion area when at least one suspicious lesion area is identified in an image frame among the plurality of image frames.

The at least one processor may refrain from obtaining a first indicator representing a probability of a first type of lesion for at least one image frame in which no suspicious lesion area is identified among the plurality of image frames.

In the landmark image acquisition operation, the processor may obtain at least two image frames, each corresponding to at least two predetermined reference positions inside the body, among the plurality of image frames.

The at least one processor may be configured to obtain a first sub-indicator representing a degree of the second type of lesion at the first reference position based on the first image frame, obtain a second sub-indicator representing a degree of the second type of lesion at the second reference position based on the second image frame, and obtain the second detection information based on the first sub-indicator and the second sub-indicator.

The at least one processor may include a first processor and a second processor, and the first processor may operate according to the first mode of operation, and the second processor may operate according to the second mode of operation.

The at least one processor may operate in the first mode of operation upon the occurrence of a first trigger event and may operate in the second mode of operation upon the occurrence of a second trigger event.

The first mode of operation may be initiated at a start of the endoscopy and may be switched to the second mode of operation upon the end of the endoscopy.

The second mode of operation may be performed whenever at least two image frames are identified or may be performed when all such image frames are identified.

The at least one processor may be configured to calculate probability corresponding to each of a plurality of predetermined reference positions based on the corresponding image frames in accordance with the landmark image acquisition operation.

The at least one processor may generate a result report for the endoscopy based on the first detection information and the second detection information.

The first type of lesion may include at least one of early gastric cancer, advanced gastric cancer, adenoma, or polyp, and the second type of lesion may include at least one of intestinal metaplasia or atrophic gastritis.

According to one embodiment of the present disclosure, an operating method of an electronic device for processing an endoscopic image may comprise: obtaining, by at least one processor in the electronic device, a plurality of image frames included in the endoscopic image; obtaining first detection information related to a first type of lesion based on at least one of the plurality of image frames in a first operating mode; and obtaining second detection information related to a second type of lesion based on at least two image frames, each corresponding to at least two predetermined reference positions inside the body in a second operating mode.

In another embodiment, an endoscopic examination system may comprise: an endoscopic device configured to obtain an endoscopic image; and at least one processor configured to obtain a plurality of image frames included in the endoscopic image, obtain first detection information related to a first type of lesion based on at least one of the plurality of image frames in a first mode of operation, and obtain second detection information related to a second type of lesion based on at least two image frames, each corresponding to at least two predetermined reference positions inside the body among the plurality of image frames in a second mode of operation.

In another embodiment, an electronic device for providing information about a landmark image may comprise: a memory configured to store instructions; and at least one processor electronically connected to the memory and configured to execute the instructions, wherein the at least one processor may play back the endoscopic image in a first area of a display, identify an image frame corresponding to a plurality of predetermined landmarks based on the endoscopic image, the landmark being defined as an anatomical reference position inside the body for lesion detection. The processor may display at least one visual display in a second area of the display based on whether the image frame corresponding to the predetermined multiple landmarks is obtained, the second area including a plurality of subareas corresponding to each of the plurality of landmarks.

The at least one processor may be configured to provide a first visual display in a first subarea corresponding to the first landmark when the first image frame corresponding to the first landmark is obtained, and to provide a second visual display, different from the first visual display, in a second subarea corresponding to the second landmark when the image frame corresponding to the second landmark is not obtained, wherein the first visual display indicates at least a portion of the first image frame, and the second visual display includes a predetermined visual effect on the second subarea.

The at least one processor may be configured to provide a first visual display to a first subarea corresponding to the first landmark when the first image frame corresponding to the first landmark is obtained, and to provide a third visual display, corresponding to the first visual display, in a second subarea corresponding to the second landmark when the second image frame corresponding to the second landmark is obtained, wherein the first visual display indicates at least a portion of the first image frame, and the third visual display indicates at least a portion of the second image frame.

The at least one processor may be configured to identify an image frame corresponding to a predetermined plurality of landmarks using a landmark detection network, and wherein the landmark detection network may obtain probability that corresponds to each of the predetermined plurality of landmarks based on each image frame included in the endoscopic image.

The at least one processor may be configured to provide feedback on a focused capture requesting additional capture for the third landmark when the third image frame corresponding to the third landmark is obtained.

The processor may be configured to provide feedback regarding missing landmarks when an image frame corresponding to a particular landmark is not obtained.

The processor may be configured to provide feedback on a missing landmark in a third area of the display, and the third area may be implemented in a portion of the first area.

The processor may be configured to activate the third area when a missing landmark is confirmed according to a predetermined condition, wherein the predetermined condition may be defined based on the location of the first landmark identified based on the endoscopic image or based on the locations of two landmarks sequentially identified based on the endoscopic image.

The at least one processor may be configured to activate the second area when an event associated with obtaining an image corresponding to a landmark occurs, wherein the second area may be implemented in a portion of the first area.

The processor may be configured to activate a fourth subarea corresponding to the fourth landmark when the fourth image frame corresponding to the fourth landmark is obtained.

According to one embodiment of the present disclosure, a method of operating an electronic device for processing an endoscopic image may comprise: playing back the endoscopic image in a first area of a display using at least one processor in the electronic device; identifying an image frame corresponding to a plurality of predetermined landmarks based on the endoscopic image, the landmarks being defined as anatomical reference positions inside the body for lesion detection. The processor may also display at least one visual indicator in a second area of the display based on whether the image frame corresponding to the plurality of predetermined landmarks is obtained, the second area including a plurality of subareas corresponding to each of the plurality of landmarks.

In another embodiment of the present disclosure, an endoscopic examination system may comprise: a display; an endoscopic device for capturing an endoscopic image; and at least one processor, wherein the at least one processor is configured to play back the endoscopic image in a first area of the display, identify an image frame corresponding to a plurality of landmarks predetermined based on the endoscopic image, the landmarks being defined as anatomical reference positions inside the body for lesion detection. The processor may also display at least one visual indicator in a second area of the display based on whether the image frame corresponding to the plurality of predetermined landmarks is obtained, the second area including a plurality of subareas corresponding to each of the plurality of landmarks.

According to one embodiment of the present disclosure, an electronic device for providing information about a lesion may comprise: a memory configured to store instructions; and at least one processor electronically connected to the memory and configured to execute the instructions. The at least one processor may analyze a plurality of image frames included in an endoscopic image to provide information about a specific lesion. The at least one processor may obtain a first image frame corresponding to a first reference position based on the endoscopic image, obtain first lesion information indicating a degree of occurrence of a specific lesion at the first reference position based on the first image frame, obtain second lesion information indicating a degree of occurrence of a specific lesion at the second reference position based on the second image frame, and provide comprehensive information about a specific lesion based on the first lesion information and the second lesion information.

The at least one processor may further identify a third image frame corresponding to a third reference position based on the endoscopic image, obtain third lesion information indicating a degree of occurrence of a specific lesion at the third reference position based on the third image frame, and provide comprehensive information about a specific lesion based on the first lesion information, the second lesion information, and the third lesion information.

The at least one processor may display the first image frame in a first area of the display and display the second image frame in a second area of the display. The first area and the second area may not overlap.

The at least one processor may display the first lesion information in an area associated with the first area and display the second lesion information in an area associated with the second area.

The at least one processor may display comprehensive information about the specific lesion using a third area of the display. The third area does not overlap with the first area and the second area.

The at least one processor may provide the first lesion information by activating the first area when the first image frame is identified and provide the second lesion information by activating the second area when the second image frame is identified.

The comprehensive information about the specific lesion may include visual information indicating a probability of occurrence of a specific lesion.

The first lesion information may include a first sub-indicator indicating a probability that the first image frame corresponds to the specific lesion, and the second lesion information may include a second sub-indicator indicating a probability that the second image frame corresponds to the specific lesion.

The at least one processor may provide comprehensive information about the specific lesion through a display by switching the display screen when the endoscopic image is played back on the display.

The at least one processor may identify the first image frame by selecting one of a plurality of image frames corresponding to the first reference position and identify the second image frame by selecting one of a plurality of image frames corresponding to the second reference position.

The at least one processor may provide feedback on the detection of a specific lesion when the degree of occurrence of a specific lesion at the first reference position, as indicated by the first lesion information, satisfies a predetermined condition.

The first image frame and the second image frame may be identified using a landmark detection network trained to detect an image corresponding to the reference position based on an endoscopic image.

According one embodiment of the present disclosure, a method of operating an electronic device for providing information about a lesion may comprise: identifying, by at least one processor included in the electronic device, a first image frame corresponding to a first reference position and a second image frame corresponding to a second reference position based on the endoscopic image; obtaining first lesion information indicating the degree of occurrence of a specific lesion at the first reference position based on the first image frame; obtaining second lesion information indicating the degree of occurrence of a specific lesion at the second reference position based on the second image frame; and providing comprehensive information about a specific lesion based on the first lesion information and the second lesion information.

In another embodiment of the present disclosure, an endoscopic examination system may be configured to identify a first image frame corresponding to a first reference position and a second image frame corresponding to a second reference position based on the endoscopic image; obtain first lesion information indicating the degree of occurrence of a specific lesion at the first reference position based on the first image frame; obtain second lesion information indicating the degree of occurrence of a specific lesion at the second reference position based on the second image frame, and provide comprehensive information about a specific lesion based on the first lesion information and the second lesion information using the display.

[System]

FIG. 1 is a diagram illustrating an embodiment of an endoscopic examination system 100 according to various embodiments.

Referring to FIG. 1, the endoscopic examination system 100 in one embodiment may include an electronic device 120 for endoscopic image analysis. The electronic device 120 is electronically connected to the endoscopic device 110. For the purpose of this description, the electronic device 120 may also be referred to as a computing device. At this time, the endoscopic device 110 and the electronic device 120 can communicate with each other via wired or wireless communication, enabling the transmission and reception of data.

The endoscopic device 110 may perform endoscopic examinations and capture image data of the esophagus, stomach, and duodenum through a capture module that is inserted into the oral cavity. The endoscopic device 110 may be used for inspection of gastrointestinal diseases (e.g., including early gastric cancer (EGC) and advanced gastric cancer (AGC)), adenomas, atrophic gastritis, reflux gastritis, reflux gastritis, malignant tumors (gastric adenocarcinoma, gastric lymphoma, gastrointestinal stromal tumor), intestinal metaplasia, reflux esophageal ulcers or duodenum ulcers.

The endoscopic device 110 may include at least one display for providing various visual information related to the endoscopic examination. The display may show the endoscopic image captured by the capture module and/or provide the results of the endoscopic examination.

The electronic device 120 may analyze the endoscopic image obtained by the endoscopic device 110 and provide its analysis information. Upon receiving the endoscopic image from the endoscopic device 110, the electronic device 120 analyze the received endoscopic image to provide the analysis information regarding potential lesions or diseases.

In particular, the electronic device 120 may analyze the endoscopic image and perform a diagnosis operation to identify various gastrointestinal diseases, including but not limited to gastric cancer (both early gastric cancer (EGC) and advanced gastric cancer (AGC)), adenoma, atrophic gastritis, reflux gastritis, malignant gastric tumors (gastric adenocarcinoma, gastric lymphoma, gastrointestinal stromal tumor), and intestinal metaplasia. In this case, the electronic device 120 performs the lesion detection based on the endoscopic images to assist in diagnosing the gastrointestinal disease.

In this disclosure, the term "lesion" is used broadly and is not limited to a specific disease. A lesion may be defined as an area in the image that appears abnormal. For example, the lesion may include areas where the mucosa protrudes from the surrounding surface (e.g., an area suspicious of being a polyp or adenoma), areas where the color of the mucosa differs from the surrounding tissue or areas with a shape similar to the intestinal mucosa identified at the specific location (e.g., an area that is suspicious of being an intestinal epithelial plasma).

The electronic device 120 may detect the lesion and analyze the lesion according to a predetermined method (e.g., classifying the lesion by a neural network model), thereby diagnosing the gastrointestinal disease corresponding to the lesion.

Accordingly, the electronic device 120 may function as a main processor of the endoscopic device 110, but it is not limited thereto. It may operate as an additional processor electronically connected to the main processor and provide additional functions such as landmark detection and lesion detection The following sections provide a detailed description of the configuration of the electronic device for endoscopic image analysis and the various functions it performs.

[Configuration of the Electronic Device]

Figure 2:
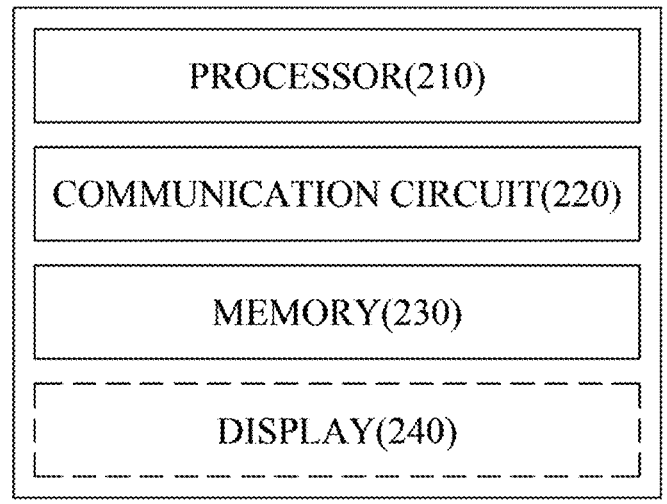
FIG. 2 is a diagram illustrating a hardware configuration of the electronic device 200 for obtaining information about gastric lesions based on endoscopic images according to various embodiments.

FIG. 2 is a diagram illustrating a hardware configuration of the electronic device 200 for obtaining information about the gastric lesion based on the endoscopic image according to various embodiments.

Referring to FIG. 2, the electronic device 200 according to one embodiment may include a processor 210, a communication circuit 220, and a memory 230. The configuration of the electronic device 200 is not limited to configuration shown in FIG. 2 and may include additional hardware or software components typically found in a general computing device or a mobile device.

The processor 210 may include at least one processor configured to provide various functions. For example, the software (e.g., program) may control at least one component (e.g., a hardware or software component) of the electronic device 200 connected to the processor 210 and may perform various data processing or computation. According to an embodiment, as at least a portion of the data processing or computation, the processor 210 may store the instruction or data received from the other component in the memory 230 (e.g., volatile memory), process the instruction or data stored in the volatile memory, and store the resultant data in the non-volatile memory. The processor 210 may include a main processor (e.g., a central processing unit (CPU) or an application processor) or an auxiliary processor (e.g., a graphic processing unit (GPU), a neural processing unit (NPU), an image signal processor (ISP), a sensor hub processor, or a communication processor) that operates independently or in conjunction with the main processor. For instance, when the electronic device 200 includes the main processor and the auxiliary processor, the auxiliary processor may be configured to use lower power than the main processor or be specific to a particular function. The auxiliary processor may be implemented separately from or in conjunction with the main processor. The auxiliary processor may control certain functions or states related to at least one component of the electronic device 200 (e.g., the display 240 or the communication circuit 220) depending on the state of the main processor (e.g., active or inactive). According to an embodiment, the auxiliary processor (e.g., the image signal processor or the communication processor) may be implemented as part of another component (e.g., the communication circuit 220) that is functionally related to the auxiliary processor. According to one embodiment, the auxiliary processor (e.g., the neural network processing unit) may include hardware specifically designed for processing artificial intelligence (AI) models. The artificial intelligence models may be generated through machine learning, which could occur on the electronic device 200 itself or on a separate server. The learning algorithm may employ various methods, including supervised learning, unsupervised learning, semi-supervised learning, or reinforcement learning. The AI model may include multiple neural network layers, such as deep neural networks (DNNs), convolutional neural networks (CNNs), recurrent neural networks (RNNs), restricted Boltzmann machines (RBMs), deep belief networks (DBNs), bidirectional recurrent deep neural network (BRDNNs), deep Q-networks, or a combination of two or more of the above. The AI model could be implemented in software, hardware, or a combination of both. Meanwhile, the operation of the electronic device 200 described below may be understood as the operation of the processor 210.

According to various embodiments, the communication circuit 220 may support establishing communication channels (e.g., wired or wireless) between the electronic device 200 and the external electronic device (e.g., the endoscope device). The communication circuit 220 may include one or more communication processors (e.g., communication chips) that facilitate wired or wireless communication. According to one embodiment, the communication circuit 220 may include a wireless communication module (e.g., a cellular or a short-range wireless communication module, or a global navigation satellite system (GNSS) communication module) and a wired communication module (e.g., a local area network (LAN) or a power line communication module). Among these communication modules, the corresponding communication module may communicate with an external electronic device (e.g., the server 10) over a first network (e.g., a short-range communication network such as Bluetooth, wireless fidelity (Wi-Fi) direct, or infrared data association (IrDA)) or a second network (e.g., a long-range communication network such as a legacy cellular network, a 5G network, a next generation communication network, the Internet, or a computer network (e.g., LAN or WAN)). These various types of communication modules may be integrated into one component (e.g., a single chip) or may be implemented as a plurality of separate components (e.g., a plurality of chips). The wireless communication module may identify or authenticate the electronic device 100 within a communication network, such as the first network or the second network, using subscriber information (e.g., an international mobile subscriber identifier (IMSI)) stored in the subscriber identification module. The wireless communication module may support 5G networks and next-generation communication technologies after 4G networks, such as new radio access technology (NR). The NR access technology may support high-capacity data transmission (enhanced mobile broadband (eMBB)), terminal power minimization and multiple terminal access (mMTC), or ultra-reliable and low-latency communications (URLLC). For example, the wireless communication module may support a high frequency band (e.g., mmWave band) to achieve a high data rate. The wireless communication module may support various technologies to ensure performance in the high frequency band, such as beamforming, massive multiple-input multiple-output (MIMO), full-dimensional MIMO (FD-MIMO), array antenna, analog beamforming, or large scale antenna. The wireless communication module may support various requirements specified in the electronic device 200, the endoscopic device, or the network system. According to one embodiment, the wireless communication module may support peak data rate (e.g., 20 Gbps or more) for eMBB implementation, loss coverage (e.g., 164 dB or less) for mMTC implementation, or U-plane latency (e.g., 0.5 ms or less or roundtrip 1 ms or less of downlink (DL) and uplink (UL), respectively) for URLLC implementation.

According to various embodiments, the memory 230 may store various data used by at least one component (e.g., the processor 210) of the electronic device 200, such as software (e.g., programs), operating system, middleware, applications, and/or the artificial intelligence model. The memory 230 may also include a volatile memory or a non-volatile memory, input data or output data for commands associated therewith.

In another embodiment, the electronic device 200 may further include a display 240 for visually providing information obtained from examination and diagnosis. The display 240 may visually provide information to the outside (e.g., a user) of the electronic device 200. The display 240 could be a display device (e.g., a monitor, a hologram device, or a projector and a control circuit for controlling the device). The display may include a touch sensor to detect a touch or a pressure sensor configured to measure the intensity of the force generated by the touch.

Further, the electronic device 200 may visually provide information obtained through the examination and the analysis on a display. Specifically, the electronic device 200 may visually present information obtained through image analysis using a display in the endoscope device (e.g., a display for showing an endoscopic image). The electronic device 200 can display analysis information by overlaying it on an endoscopic image on a display integrated with the endoscopic device.

[Functions Provided by the Electronic Device]

Figure 3:
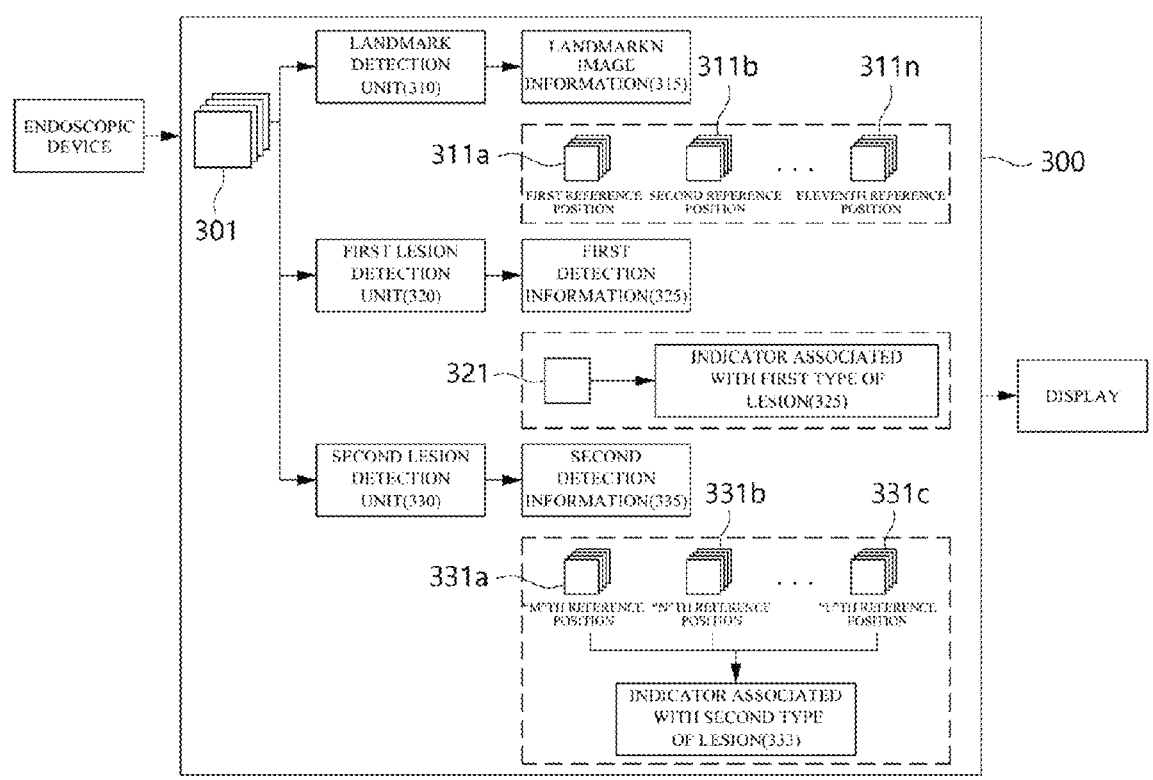
FIG. 3 is a diagram illustrating various functions for an electronic device for providing information about a lesion based on an endoscopic image, according to various embodiments.

FIG. 3 is a diagram illustrating various functions for the electronic device to provide information about lesions based on the endoscopic image, according to various embodiments.

Referring to FIG. 3, the electronic device 300 in an embodiment of the present disclosure may obtain a plurality of image frames 301 based on the endoscopic image obtained by the endoscopic device.

The electronic device 300 may include at least one processor configured to analyze the plurality of image frames 301 and provide various types of analysis information.

For example, the electronic device 300 may include a landmark detection unit 310 for detecting an image frame corresponding to a landmark among the plurality of image frames 301, a first lesion detection unit 320, and a second lesion detection unit 330 for detecting or confirming various lesions.

The landmark detection unit 310 (or the first processor) may obtain landmark image information 315 based on the analysis of at least one of the plurality of image frames 301. The landmark image information 315 may include information about an image frame corresponding to a plurality of landmarks (or reference positions). For example, the landmark image information 315 may include information about an image frame corresponding to a series of reference positions (e.g., first through eleventh reference positions) among the plurality of image frames 301. The plurality of image frames may correspond to a specific reference position. The plurality of image frames corresponding to the specific reference position may be defined as a landmark image group. For example, the landmark image information 315 may include a first landmark image group 311a corresponding to the first reference position, a second landmark image group 311b corresponding to the second reference position, and a landmark image group 311n corresponding to the eleventh reference position.

The method for obtaining landmark image information by the landmark detection unit 310 is further described with reference to FIGS. 4 through 9.

The first lesion detection unit 320 may obtain first detection information 325 for a first type of lesion based on the analysis of at least one of the plurality of image frames 301. The first type of lesion may be defined as a lesion that can be confirmed based on an image frame. That is, the first type of lesion may also mean a lesion that can specify the location and area of the corresponding lesion. For example, the first type of lesion may mean a type of lesion that can be judged by a single image of any location inside the stomach, such as a suspicious gastric cancer lesion, an adenoma lesion, or a polygon.

The second lesion detection unit 330 may obtain second detection information 335 for the second type of lesion based on the analysis of at least one of the plurality of image frames 301. The second type of lesion may be defined as a lesion that can be identify through the analysis of multiple image frames. Although an area suspicious of being a second type of lesion may be detected in a single image frame, it is difficult to specify the location and area of the corresponding lesion in the single image frame. Thus, the precise location and extent of the second type of lesion may be determined by analyzing multiple images from different locations. For example, the second type of lesion may refer to a type of lesion that can be judged by two or more images inside the stomach, such as suspicious intestinal metaplasia lesions and suspicious atrophic gastritis lesions.

The method for obtaining lesion detection information by the first lesion detection unit 320 and the second lesion detection unit 330 are described with reference to FIGS. 10 to 21.

The electronic device 300 performs a diagnosis operation based on the lesion detection information, and reports diagnosis information (e.g., an endoscopic examination result report) concerning gastrointestinal diseases.

The gastrointestinal disease may include gastric cancer (including early gastric cancer (EGC) and advanced gastric cancer (AGC)), atrophic gastritis, reflux gastritis, malignant tumors of headache gastritis (e.g., gastric adenocarcinoma, gastric lymphoma, gastrointestinal stromal tumor), and intestinal metaplasia.

The electronic device 300 may display detection information or diagnosis information via a graphical user interface (GUI) on a display. In addition, the display for providing the detection information may be the same as the one used for playing back endoscopic images captured by the endoscopic device.

[Landmark Detection and Provision of Landmark Information]

In this disclosure, the landmark may be defined as an anatomical reference location inside the body for lesion detection. Specifically, the landmark may include 11 anatomical locations across the esophagus, stomach and duodenum. For example, the landmarks may be esophagus, gastroesophageal junction, duodenum, septum, and various areas of the stomach (e.g., gastric body, fundus, cardia). It can include 11 reference positions of gastric fundus, gastric cardia and gastric body. The names of these landmarks are not limited to the terms listed herein and may include the anatomical terms commonly used in the medical community (e.g. proximal esophagus, distal esophagus, z-line, diaphragmatic indentation, cardia and fundus, corpus in anterior view including lesser curvature, corpus in posterior view including greater curvature, angulus in partial inversion, antrum, duodenal bulb, second part, and greater papilla).

Figure 4:
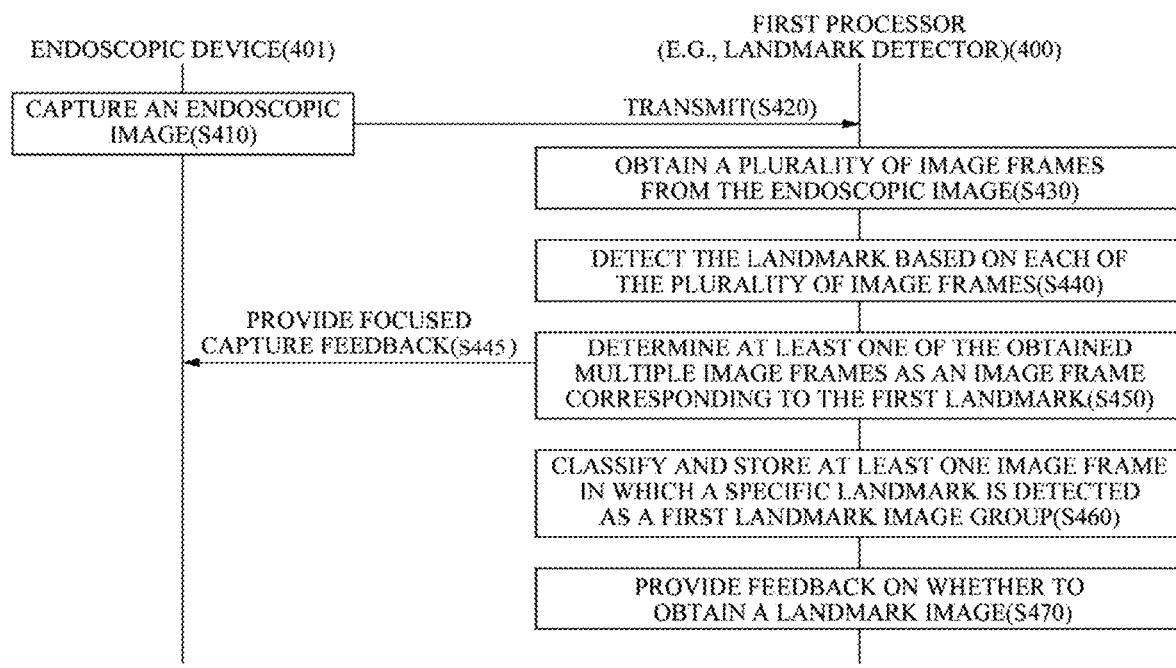
FIG. 4 is a flowchart illustrating an embodiment in which an electronic device obtains a landmark image based on an endoscopic image, according to various embodiments.

FIG. 4 is a flowchart illustrating an embodiment in which an electronic device obtains a landmark image based on an endoscopic image according to various embodiments.

Referring to FIG. 4, the endoscopic device 401 may capture an endoscopic image (s410) and can either store the endoscopic image using an image capture module or transmit it externally.

The endoscopic device 401 may transmit the endoscopic image to the first processor 400 (e.g., landmark detector) of the electronic device via a communication circuit (s420).

The first processor 400 may obtain a plurality of image frames from the endoscopic image (s430). These image frames may include all of the image frames included in the endoscopic image or may include at least some of the image frames included in the endoscopic image. Further, the plurality of image frames may be obtained by pre-processing the image frames included in the endoscopic image. That is, the first processor 400 may obtain the plurality of image frames based on at least one of all the image frames included in the endoscopic image, at least some of the image frames included in the endoscopic image, or the image frame that pre-processed the image frame included in the endoscopic image.

The first processor 400 may detect the landmark based on each of the plurality of image frames (s440).

This step may be performed using a landmark detection network. Specifically, the landmark detection network is a learning network including a neural network such as a convolutional neural network (CNN). The first processor 400 may detect the landmark using the landmark detection network in which the learning is completed. The first processor 400 may identify whether a particular image frame corresponds to a specific landmark using the landmark detection network learned based on the image corresponding to the plurality of landmarks.

The first processor 400 may obtain an output value indicating a probability that each image frame corresponds to at least one landmark using the landmark detection network. For example, the first processor 400 may determine if the output value indicates gastric cardia or pylorus among the predefined landmarks, or if the output value indicates none of the predefined landmarks.

More specifically, the first processor 400 may calculate the probability associated with each landmark for each of the plurality of image frames. That is, the first processor 400 may obtain the output values corresponding to the number of the multiple landmarks based on each of the multiple image frames. For example, the first processor 400 may obtain a first output value indicating the probability that the first image frame corresponds to the first landmark and a second output value indicating the probability that the first image frame corresponds to the second image frame by inputting the first image frame to the landmark detection network (or landmark detector).

In this case, the first processor 400 can obtain the landmark information corresponding to the image frame based on the obtained output values. In particular, the first processor 400 may identify the highest maximum output value among the obtained multiple output values. The first processor 400 may determine a specific landmark corresponding to the maximum output value as a landmark corresponding to the image frame. However, the first processor 400 may perform a secondary verification based on a predetermined threshold to determine if the landmark does not correspond to none of them. For example, if the maximum output value is equal to or greater than the predetermined threshold, the first processor 400 may determine the specific landmark corresponding to the maximum output value as a landmark corresponding to the image frame. If the maximum output value is less than the predetermined threshold, the first processor 400 may determine that there is no landmark corresponding to the image frame.

The first processor 400 may determine at least one of the obtained multiple image frames as an image frame corresponding to the first landmark (S450).

In this case, the first processor 400 may provide focused capture feedback to the endoscope device 401 for the location (first landmark) (S [440] 445). The first processor 400 may provide an audible alarm via a speaker, a visual alarm via a display, or a tactile alarm via a vibration lamp. For example, if the first image frame corresponds to the first landmark, the first processor 400 may display a message requesting the focused capture of the location through the display.

The first processor 400 may determine, based on the landmark information from the sequentially obtained image frames, whether to provide feedback for the focused capture. Specifically, the first processor 400 may determine an operation to be performed by comparing the landmark corresponding to the first output value and the landmark corresponding to the second output value, each output value corresponding to the sequentially obtained first image frame and the second image frame.

For example, if the landmark corresponding to the first output value differs from the landmark corresponding to the second output value, the first processor 400 may perform the focused capture feedback operation by determining that the landmark corresponding to the second output value is obtained first. Since the landmark is an important location in determining gastrointestinal disease, it is necessary to capture sufficient images of specific landmarks. The first processor 400 can obtain a plurality of images for a specific landmark by requesting the focused capture of the specific landmark when the endoscope device captures the image for the specific landmark.

On the contrary, if the landmark corresponding to the first output value and the landmark corresponding to the second output value are the same, the first processor 400 may refrain from operating the focused capture feedback operation by determining that the focused capture for the same landmark is being performed.

The first processor 400 may classify and store at least one image frame in which a specific landmark is detected as a first landmark image group (S460). For example, the first processor 400 may classify the first image frame corresponding to the first landmark as a first landmark image group and store in memory. In this case, the first processor 400 may group images corresponding to each of the multiple landmarks together and store them in memory. The processor 400 may provide the grouped images to users by storing in folders corresponding to each of the multiple landmarks.

In addition, the first processor 400 may provide feedback on whether to obtain a landmark image (s470).

Specifically, the first processor 400 may provide feedback on the missing landmark if there is a landmark which the image corresponding to the multiple landmarks is not obtained.

Further, even if the image corresponding to the specific landmark is obtained, the first processor 400 may provide feedback for requesting additional capture of the specific landmark if the quality of the obtained image is insufficient for analysis.

For example, after the endoscopic examination, the first processor 400 may provide feedback on the missing image if the multiple image frames obtained from the endoscopic images do not include the image corresponding to the specific landmark.

In addition, without limitation, the first processor 400 may provide feedback on the missing landmark during the examination if the landmark predicted to be obtained is not captured as the endoscopic examination proceeds.

Figure 5:
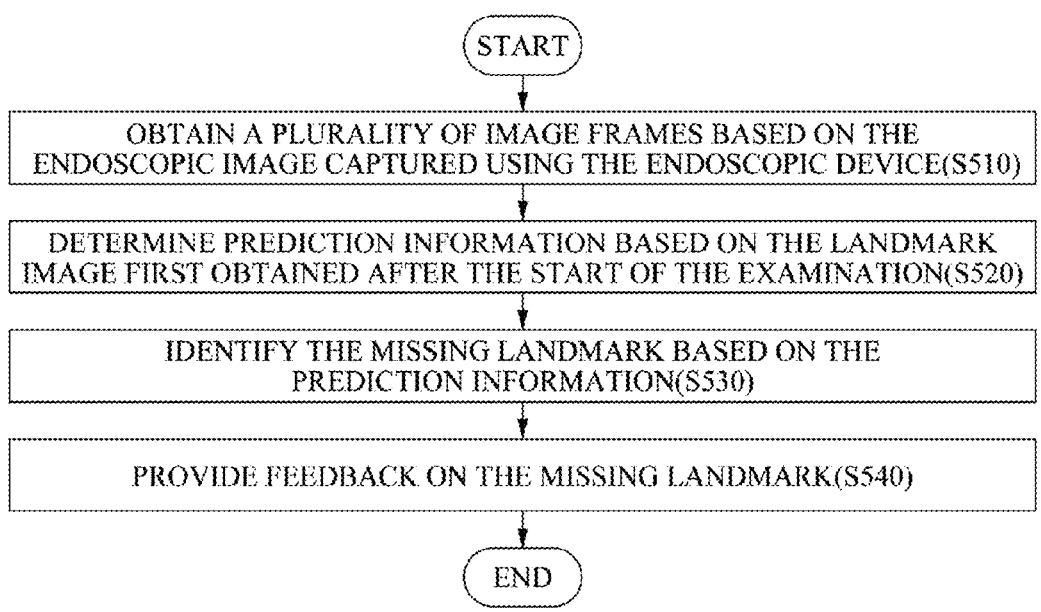
FIG. 5 is a flowchart illustrating an example of a method in which an electronic device provides feedback on whether or not to obtain a landmark image during an endoscopic examination, according to various embodiments.

FIG. 5 is a flowchart illustrating an example of a process in which the electronic device provides feedback on whether to obtain a landmark image during the endoscopic examination, according to various embodiments.

Referring to FIG. 5, the electronic device (or at least one processor in the electronic device) may obtain a plurality of image frames based on the endoscopic image captured using the endoscopic device (s510).

The electronic device may determine prediction information based on the landmark image first obtained after the start of the examination (s520). Here, the prediction information may include the currently ongoing examination location or the future examination path. The electronic device can predict the location at which the examination is started by confirming the landmark image which is first obtained after the start of the examination. This is because the landmark at which the image is to be obtained may be inferred in a time series according to the location at which the endoscopic examination is first started. That is, the electronic device may obtain prediction information including at least one of the locations of the landmarks to be obtained or the future examination path to be proceeded on the basis of the landmark location corresponding to the landmark image first obtained after the start of the examination.

The electronic device may identify the missing landmark based on the prediction information (s530). In particular, when the image corresponding to the specific landmark expected to be captured is not obtained in a predetermined method, the electronic device may determine that the specific landmark is missing.

For example, if the first image corresponding to the first landmark is obtained after the start of examination, the electronic device may predict that the image corresponding to the second landmark is obtained after the start of examination. In this case, when the third image corresponding to the third landmark is obtained after the first image is captured, the electronic device may determine that the image corresponding to the second landmark is missing.

In addition, the electronic device can identify the missing landmark based on two consecutively obtained landmark images. In this case, even if the first obtained landmark image is not identified, the electronic device may determine information about the landmark that is expected to be obtained.

For example, if the second image corresponding to the second landmark is obtained after the first image corresponding to the first landmark is obtained, the electronic device may determine that the image corresponding to the third landmark is missing.

The electronic device may provide feedback on the missing landmark (s540).

Figure 6:
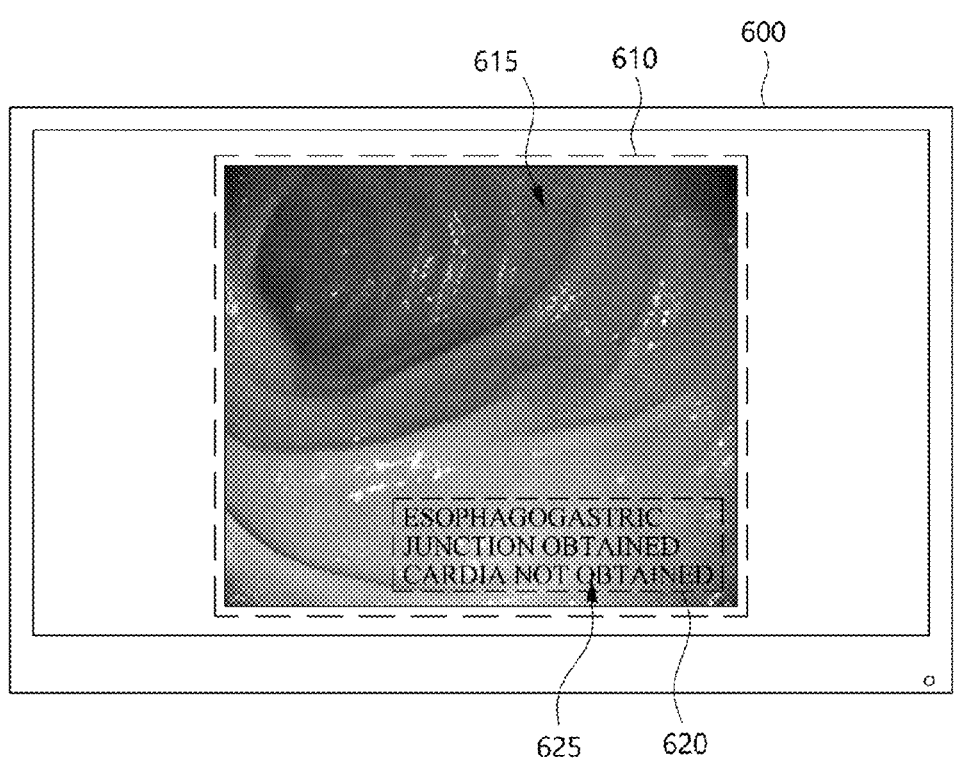
FIG. 6 is a diagram illustrating an embodiment in which an electronic device provides feedback on whether or not to obtain a landmark via a display, according to various embodiments.

FIG. 6 is a diagram illustrating an embodiment where an electronic device provides feedback on whether to obtain a landmark through a display according to various embodiments.

Figure 7:
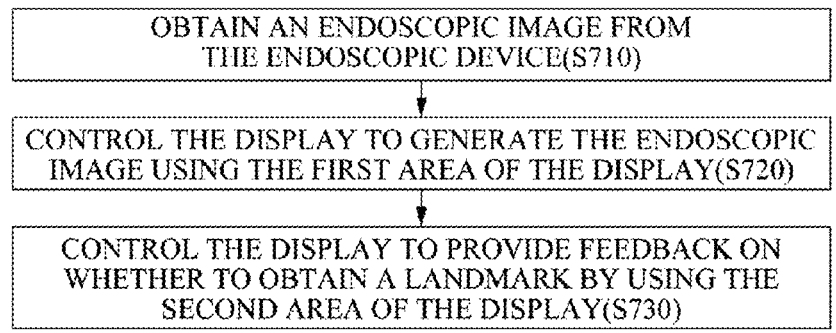
FIG. 7 is a flowchart illustrating an embodiment in which an electronic device provides feedback on whether to obtain a landmark through a display according to various embodiments.

FIG. 7 is a flowchart illustrating an embodiment where an electronic device provides feedback on whether to obtain a landmark through a display according to various embodiments.

Referring to FIG. 7, the electronic device may obtain an endoscopic image from the endoscopic device (s710). In addition, the electronic device may control the display to generate the endoscopic image using the first area of the display (s720). The electronic device may control the display to provide feedback on whether to obtain a landmark by using the second area of the display (s730).

For example, with reference to FIG. 6, the electronic device may output an endoscopic image 615 using the display 600. The electronic device may control the display 600 to play back the endoscopic image 615 using the first area 610 of the display.

In addition, the electronic device may provide feedback information 625 on whether to obtain a landmark image by using the display 600. The electronic device may provide feedback information 625 related to whether to obtain a landmark image by using the second area 620 of the display. In this case, the second area 620 may be implemented in at least a portion of the first area 610. The second area 620 may be within the first area 610. For example, the electronic device may output a message indicating whether to obtain a landmark image on a display. Specifically, when an image corresponding to a particular landmark is obtained, the electronic device may output a message informing of the acquisition of the landmark image (e.g., "esophagogastric junction obtained"). In addition, when an image corresponding to a specific landmark is not obtained, the electronic device may output a message informing that the landmark image is not obtained (e.g., "cardia not obtained").

When a predetermined event occurs, the electronic device may activate the second area 620 to provide feedback information about whether a landmark is obtained. Specifically, when an image corresponding to a particular landmark is obtained, the electronic device may activate the second area 620 to display a message indicating that the landmark has been obtained. In addition, if an image corresponding to a particular landmark is not obtained, the electronic device may activate the second area 620 to display a message indicating that the landmark is not obtained. In addition, when a user input requesting confirmation of whether a landmark has been obtained is received, the electronic device may activate the second area 620 to display feedback information indicating whether a landmark is obtained.

Figure 8:
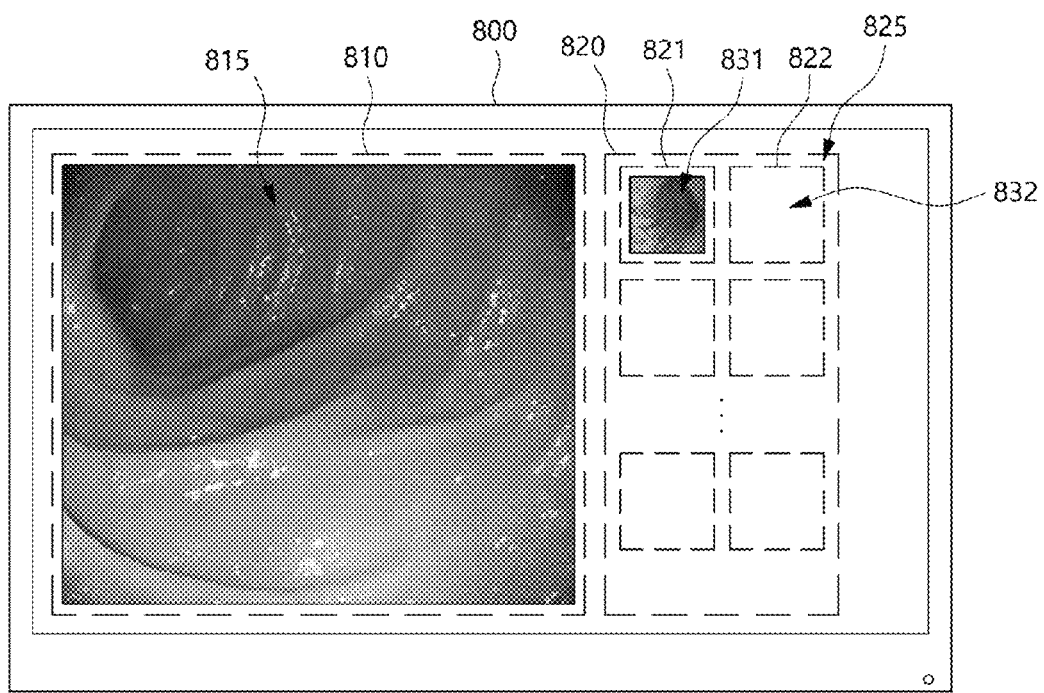
FIG. 8 is a diagram illustrating another embodiment in which an electronic device provides feedback on whether to obtain a landmark through a display according to various embodiments.

FIG. 8 is a diagram illustrating another embodiment where an electronic device provides feedback on whether to obtain a landmark through a display, according to various embodiments.

Figure 9:
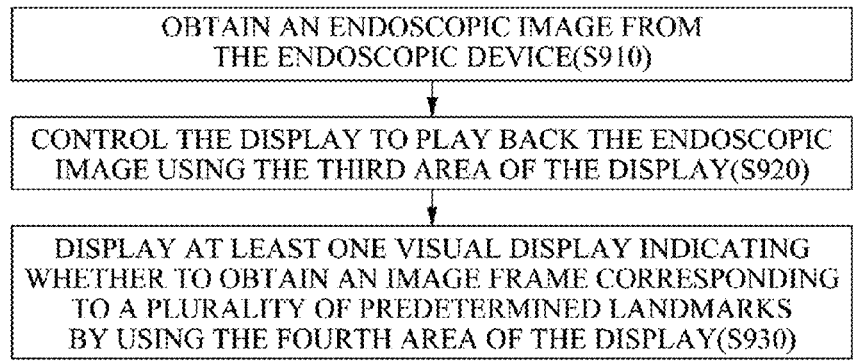
FIG. 9 is a flowchart illustrating another embodiment in which an electronic device provides feedback on whether to obtain a landmark through a display according to various embodiments.

FIG. 9 is a flowchart illustrating another embodiment where an electronic device provides feedback on whether to obtain a landmark through a display, according to various embodiments.

Referring to FIG. 9, the electronic device may obtain an endoscopic image from the endoscopic device (s910). In addition, the electronic device may control the display to play back the endoscopic image using the third area of the display (s920). In addition, the electronic device may display at least one visual display (or indicator) indicating whether to obtain an image frame corresponding to a plurality of predetermined landmarks by using the fourth area of the display (s930).

For example, with reference to FIG. 8, the electronic device may output an endoscopic image 815 using the display 800. The electronic device may control the display 800 to generate the endoscopic image 615 by using the third area 810 of the display.

In addition, the electronic device may provide at least one visual display indicating whether to obtain an image corresponding to a plurality of landmarks by using the display 800. The electronic device may display landmark information 825 including at least one visual display indicating whether to obtain an image corresponding to a plurality of landmarks using the fourth area 820 of the display.

In this case, the fourth area 820 may include multiple subareas corresponding to each of the plurality of landmarks. For example, the fourth area 820 may include a first subarea 821 corresponding to the first landmark and a second subarea 822 corresponding to the second landmark.

For example, when the first image frame corresponding to the first landmark is obtained, the electronic device may provide the first visual display 831 using the first subarea 821 corresponding to the first landmark. In this case, the first visual display 831 may be a display indicating that an image corresponding to the first landmark has been obtained. As a specific example, the first visual display 831 may be implemented based on at least a portion of the first image frame corresponding to the first landmark. Alternatively, the first visual display 831 may be an image captured from image frames in which the first landmark is identified in the endoscopic image.

Additionally, for example, if an image frame corresponding to the second landmark is not obtained, the electronic device may provide a second visual display 832 different from the first visual display to the second subarea 822 corresponding to the second landmark. In this case, the second visual display may indicate that the image frame corresponding to the landmark is not obtained. The second visual display 832 may be provided as a blank image as shown in FIG. 8, but is not limited thereto, and an image obtained by black and white processing of the corresponding landmark image, a text indicating the name of the corresponding landmark, or a visual effect that visually emphasizes the second subarea 822 to be prominent.

In this case, when the electronic device obtains a second image frame corresponding to the second landmark, the electronic device may provide a third visual display (not shown) corresponding to the first visual display to the second subarea 822 corresponding to the second landmark. In this case, the third visual display (not shown) may be a visual display determined in the same manner as the first visual display 821. For example, the third visual display may be implemented based on at least a portion of the second image frame corresponding to the second landmark.

In addition, when a predetermined event occurs, the electronic device may activate the fourth area 820 that provides information about whether to obtain an image corresponding to a plurality of landmarks. Specifically, when a predetermined event occurs, the electronic device may provide landmark information 825 by activating the fourth area 820 in at least a portion of the third area 810. Additionally, when a predetermined event occurs, the electronic device may provide landmark information 825 by activating a fourth area 820 that does not overlap with the third area 810. For example, when an image corresponding to a particular landmark is captured, the electronic device may activate the fourth area 820 to provide a visual display in a subarea corresponding to the particular landmark.

In addition, the electronic device may activate at least a portion of the plurality of subareas included in the fourth area 820 according to the obtained landmark. For example, when an image corresponding to a specific landmark is obtained, the electronic device may activate a subarea corresponding to the specific landmark and provide a visual display for the subarea.

The following describes the operation of an electronic device for detecting a gastric lesion by an image analysis algorithm and providing information about the gastric lesion or gastrointestinal disease.

[Detection of Gastric Lesions and Provision of Gastric Lesion Information]

Figure 10:
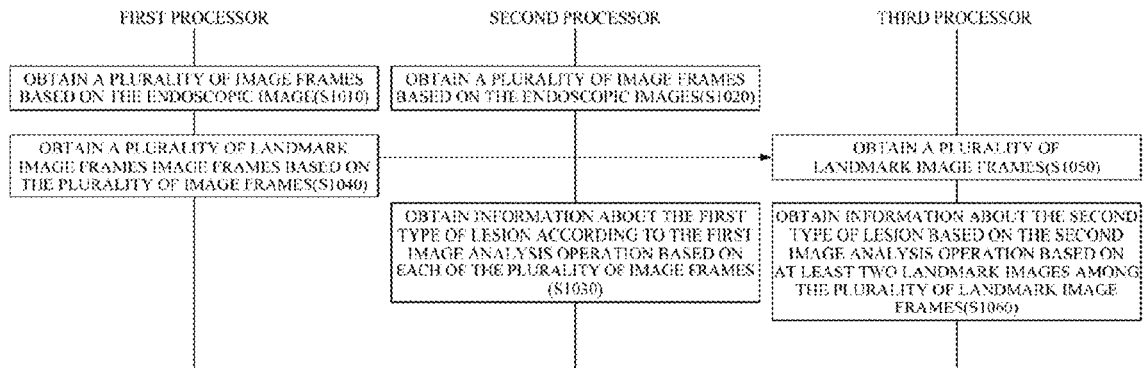
FIG. 10 is a diagram describing a method of obtaining lesion information performed by at least one processor included in an electronic device according to various embodiments.

FIG. 10 is a diagram illustrating a method of obtaining a lesion information performed by at least one processor in an electronic device according to various embodiments.

In one embodiment, the electronic device may obtain gastric lesion information from the endoscopic images by performing a plurality of image processing operations using at least one processor. For example, the electronic device may include a first processor for checking an image corresponding to a landmark based on an endoscopic image, a second processor for checking a first type of lesion based on an endoscopic image, and a third processor for checking a second type of lesion based on an endoscopic image (or landmark images). In this case, the first processor, the second processor and the third processor may be separate components, but not limited thereto. These processors may represent logically distinct operations performed in the processor. The definitions of the first type of lesion and the second type of lesion are described above in this disclosure and incorporated by reference.

For example, referring to FIG. 10, the first processor in the electronic device may obtain a plurality of image frames based on the endoscopic image (s1010). In addition, the first processor may obtain a plurality of landmark image frames based on the plurality of image frames (s1040). In this case, the landmark image frame means at least one image frame corresponding to a plurality of predetermined landmarks. The landmark image acquisition operation performed by the first processor may have the same technical features described in FIGS. 4 to 9 above.

In addition, the second processor in the electronic device may obtain a plurality of image frames based on the endoscopic images (s1020). That is, a plurality of image frames obtained based on the endoscopic image (or included in the endoscopic image) may be input to a first processor for confirming the landmark image and a second processor for confirming the first type of lesion, respectively.

In addition, the second processor may obtain information about the first type of lesion according to the first image analysis operation based on each of the plurality of image frames (S1030). At this time, the information about the first type of lesion may include at least one or more of the presence or absence of the first type of lesion, the probability of responding to the first type of lesion, the type of the first type of lesion, or the visual information about the location of the first type of lesion.

Details of the first image analysis operation performed by the second processor are described below.

In addition, the third processor in the electronic device may obtain a plurality of landmark image frames (S1050). In this case, the plurality of landmark image frames obtained by the third processor may be the plurality of landmark image frames identified by the first processor. That is, the electronic device may be set to input a plurality of landmark image frames obtained by the first processor to the third processor.

Further, the third processor may obtain information about the second type of lesion based on the second image analysis operation based on at least two landmark images among the plurality of landmark image frames (S1060). In this case, the information about the second type of lesion may include at least one or more of the presence or absence of the second type of lesion, the probability of responding to the second type of lesion, the type of the second type of lesion, or the visual information about the location of the second type of lesion.

Details of the second image analysis operation performed by the third processor are described below.

[Detection of a First Type of Lesion]

Figure 11:
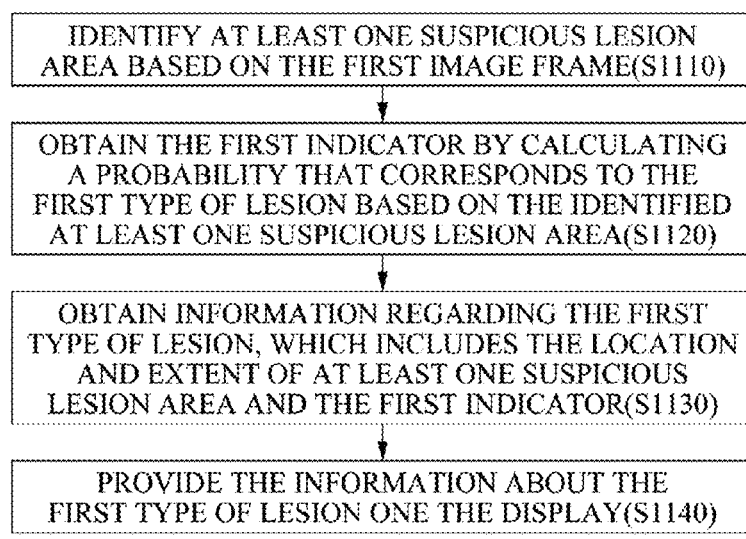
FIG. 11 is a diagram illustrating a first image analysis operation for an electronic device to provide information about a first type of lesion, according to various embodiments.

FIG. 11 is a diagram illustrating a first image analysis operation for an electronic device to provide information about a first type of lesion, according to various embodiments.

Referring to FIG. 11, the electronic device, or at least one processor in the electronic device, may identify at least one suspicious lesion area based on the first image frame (s1110). In this case, the first image frame may refer to an image frame that is the target of the first image analysis operation among the plurality of image frames included in the endoscopic image. Specifically, the electronic device may identify at least one suspicious lesion area by, using a pre-stored image segmentation model, segmenting an area representing a characteristic of the lesion from each image frame (e.g., the first image frame) in the endoscopic image. Alternatively, the electronic device may identify at least one suspicious lesion area by, using a pre-stored image filtering model (e.g., a kernel filtering model, etc.), specifying an area representing a characteristic of the lesion in each image frame (e.g., the first image frame) included in the endoscopic image.

In addition, the electronic device may obtain the first indicator by calculating a probability that corresponds to the first type of lesion based on the identified at least one suspicious lesion area (s1120). In this case, the first indicator refers to a numerical value or indicator indicating a probability that corresponds to the first type of lesion. Specifically, the electronic device may obtain the first indicator by, using a classification model, calculating a probability that at least one suspicious area corresponds to a plurality of first types of lesions. For example, the electronic device may obtain the first indicator by calculating a probability that at least one suspicious area corresponds to an adenoma, a probability that corresponds to an early gastric cancer, a probability that corresponds to an advanced gastric cancer, or a probability that corresponds to a malignant tumor, and so on. In this case, the electronic device can determine the probability value having the highest value among the plurality of probability values as the first indicator.

In addition, the electronic device may obtain information regarding the first type of lesion, which includes the location and extent of at least one suspicious lesion area and the first indicator. (s1130). The at least one suspicious area information may include a location of the suspicious area or a range of the suspicious area.

In addition, the electronic device may provide the information about the first type of lesion one the display (s1140). Specifically, the electronic device may visually provide the information about the first type of lesion to the user on the display. In this case, the electronic device may provide information about the first type of lesion through a user interface implemented in the electronic device or a display environment where the endoscopic image is played back.

Figure 12:
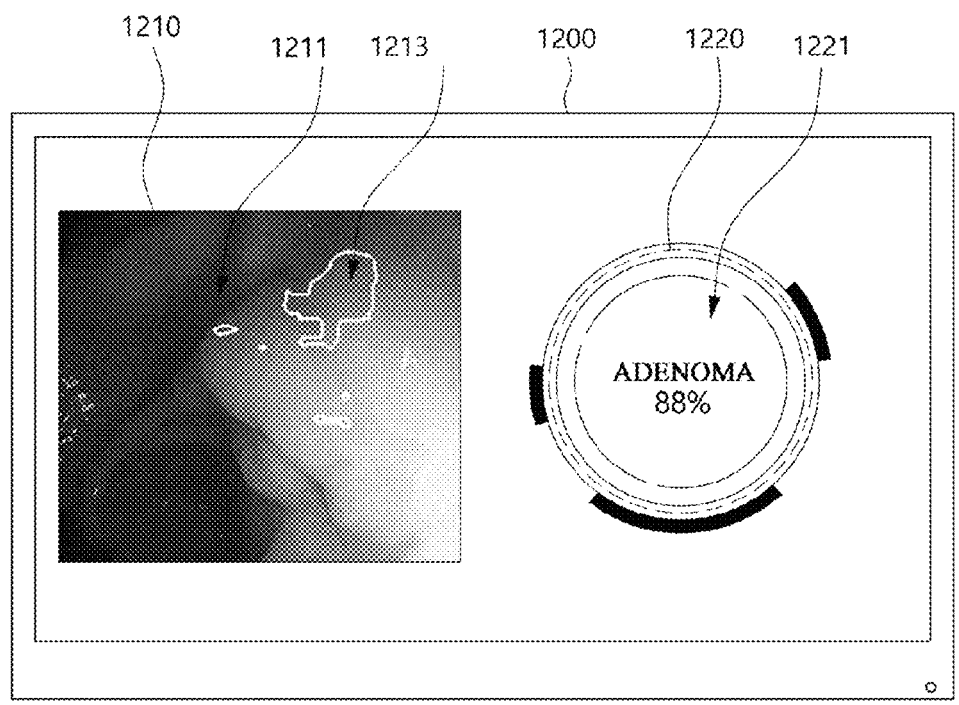
FIG. 12 is a diagram illustrating an example of an electronic device providing information about a first type of lesion, according to various embodiments.

FIG. 12 is a diagram illustrating an example of the electronic device providing information about the first type of lesion according to various embodiments.

Referring to FIG. 12, the electronic device may provide the endoscopic image and first detection information associated with the first type of lesion on a display 1200. The first detection information may include information about the first type of lesion.

The electronic device may control the display 1200 to display the first image frame 1211 in a first area 1210 of the display. In this case, the first image frame 1211 may be an image frame included in the endoscopic image. That is, the electronic device may control the display 1200 to stop playing back the endoscopic image and display the first image frame 1211 in the first area 1210 when a lesion is detected during the playback of the endoscopic image.

The electronic device may obtain the information about the first type of lesion by analyzing the first image frame 1211. In addition, the electronic device may provide the information 1213 and 1221 on the first type of lesion on the display 1200.

For example, the electronic device may provide information about at least one suspicious area 1213 related to the first type of lesion in a second area (not shown) of the display. The second area may be a portion of the first area 1210. In this case, the first image frame 1210 may be an area corresponding to at least one suspicious area associated with the first type of lesion.

In addition, upon the occurrence of a predetermined event, the electronic device may activate the second area to display information about the first type of lesion. In this case, the range of the second area may correspond to the range of the at least one suspicious area. For example, when the electronic device detects at least one suspicious area in a specific image frame, the electronic device may activate the second area by displaying a visual effect on the at least one suspicious area.

The electronic device may provide information about at least one suspicious area 1213 by displaying a visual effect (e.g., boundary marking or highlighting) on the at least one suspicious area identified in the first image frame 1211.

As another example, the electronic device may provide the first indicator 1221 indicating the probability that corresponds to the first type of lesion in a third area 1220 of the display. In this case, the third area 1220 may be positioned separately from the first area 1210 but could overlap with a portion of the first area 1210 if necessary.

In addition, upon the occurrence of a predetermined event, the electronic device may activate the third area 1220 to provide information about the first type of lesion. For example, when the electronic device identifies at least one suspicious area in a particular image frame after playback of endoscopic image, the electronic device may activate the third area 1220 to provide information about the first type of lesion.

For example, the electronic device may provide the first indicator 1221 as text (e.g., 88% probability of adenoma) indicating the likelihood that the suspicious area corresponds to at least one first type of lesion.

[Detection of a Second Type of Lesion]

According to the present disclosure, "the second type of lesion" may be a lesion that lacks a clearly defined boundary with the surrounding mucosa. For example, "intestinal metaplasia" (IM), which is a precursor stage of gastric cancer, may be one of the second type of lesions of the present disclosure. In this case, the type of intestinal metaplasia can be defined in histopathology according to morphological features or mucus content of xanthoma cells.

In order to detect the second type of lesion based on the endoscopic image, it is necessary to analyze an image of a histopathologically or anatomically important location inside the body. For example, in order for the electronic device to detect the second type of lesion based on the endoscopic image, it is necessary to analyze the image of the antrum above and the image of the corpus above. That is, the electronic device can detect the second type of lesion based on multiple images corresponding to various locations inside the body.

Figure 13:
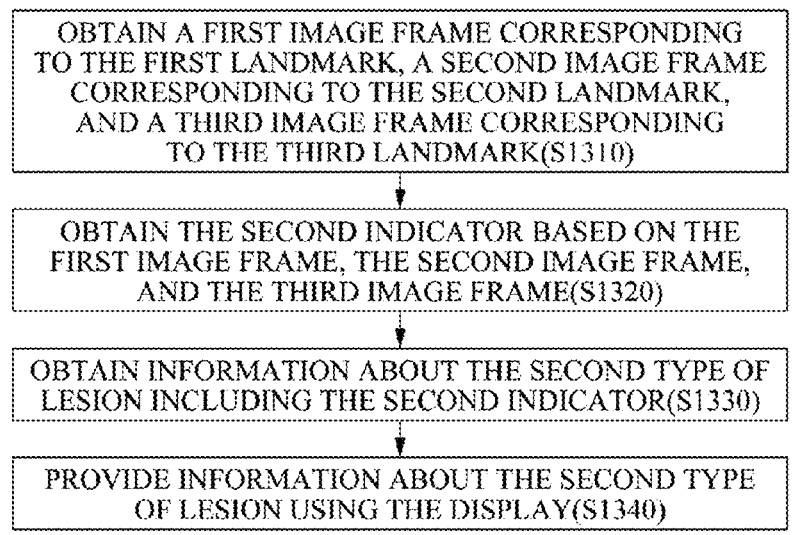
FIG. 13 is a diagram illustrating a second image analysis operation for an electronic device to provide information about a second type of lesion, according to various embodiments.

FIG. 13 is a diagram illustrating a second image analysis operation for the electronic device to provide information about the second type of lesion according to various embodiments.

To obtain the information about the second type of lesion, the electronic device may use an image corresponding to at least two predetermined landmarks. More specifically, the electronic device may identify the second type of lesion based on the images of the three predetermined landmarks, and it may predict gastrointestinal diseases such as intestinal metaplasia based on the image.

Referring to FIG. 13, the electronic device may obtain a first image frame corresponding to the first landmark, a second image frame corresponding to the second landmark, and a third image frame corresponding to the third landmark (s1310).

In addition, the electronic device may obtain the second indicator based on the first image frame, the second image frame, and the third image frame (s1320). In this case, the second indicator may indicate a probability that the second type of lesion corresponds to the second type of lesion. In particular, the second indicator may indicate the presence or absence of the second type of lesion or the level of the second type of lesion of the endoscopic examination target. That is, the electronic device may obtain the indicator of the second type of lesion based on at least two or more landmark images.

A detailed method of calculating the second indicator by the electronic device is described with reference to FIGS. 14 and 15.

Figure 14:
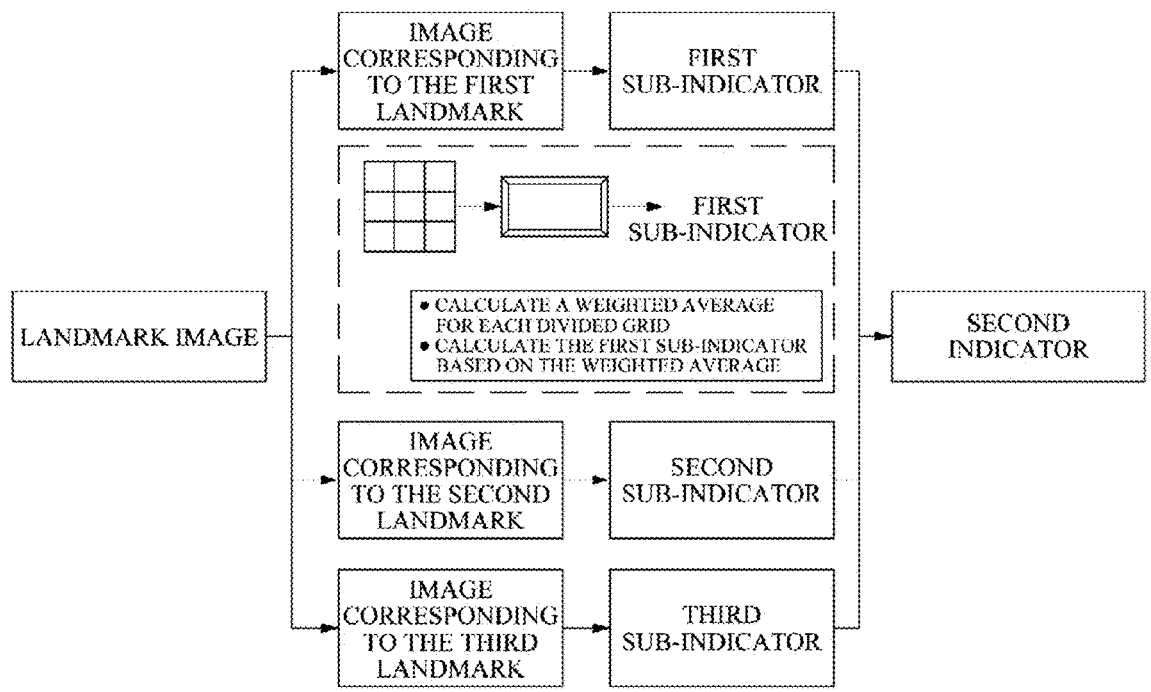
FIG. 14 is a diagram illustrating an embodiment for an electronic device to obtain a second indicator based on a plurality of landmark images, according to various embodiments.

FIG. 14 is a diagram illustrating an embodiment for the electronic device to obtain the second indicator based on a plurality of landmark images according to various embodiments.

Referring to FIG. 14, the electronic device may obtain the second indicator associated with the second type of lesion based on the landmark image.

Specifically, the electronic device may obtain the second indicator associated with the second type of lesion based on the first image corresponding to the first landmark, the second image corresponding to the second landmark, and the third image corresponding to the third landmark. In this case, the first landmark, the second landmark and the third landmark may be predetermined inside the body.

In addition, the electronic device may obtain the second indicator by calculating a sub-indicator, indicating a probability that corresponds to the second type of lesion, for each of multiple landmark images. The operation of calculating the sub-indicator may be an operation to process a plurality of landmark images to obtain an indicator associated with a second type of lesion. At this time, the sub-indicator associated with the second type of lesion may indicate the probability of occurrence of the second type of lesion. For example, the sub-indicator may be selected from one of a plurality of result values (e.g., severe, moderate, etc.) indicating the level of the second type of lesion.

That is, the electronic device may calculate a sub-indicator indicating the probability of responding to the second type of lesion based on a landmark image.

For example, the electronic device may obtain a first sub-indicator based on a first image corresponding to the first landmark, obtain a second sub-indicator based on a second image corresponding to the second landmark, and obtain a third sub-indicator based on a third image corresponding to the third landmark.

A specific method for calculating a sub-indicator related to the second type of lesion based on the landmark image is as follows.

The electronic device may calculate a sub-indicator indicating whether or not the second type of lesion is suspicious by identifying at least one area having a pattern corresponding to the second type of lesion in the landmark image.

In particular, the electronic device may calculate a sub-indicator indicating the probability that corresponds to the second type of lesion by dividing and analyzing the image into a plurality of areas using a neural network model. For example, the electronic device may divide the first landmark image into a plurality of grids (segments) using a neural network model, calculate a weighted average for each divided grid, and calculate the first sub-indicator based on the weighted average.

The electronic device may obtain a second indicator associated with the second type of lesion based on a plurality of sub-indicators corresponding to each of the plurality of landmark images. For example, the electronic device may obtain the second indicator by calculating an average of a plurality of sub-indicators. Alternatively, the electronic device may obtain the second indicator by calculating a corresponding probability value of the second type based on the plurality of sub-indicators. Alternatively, the electronic device may provide information about a plurality of sub-indicators as the second indicator.

Figure 15:
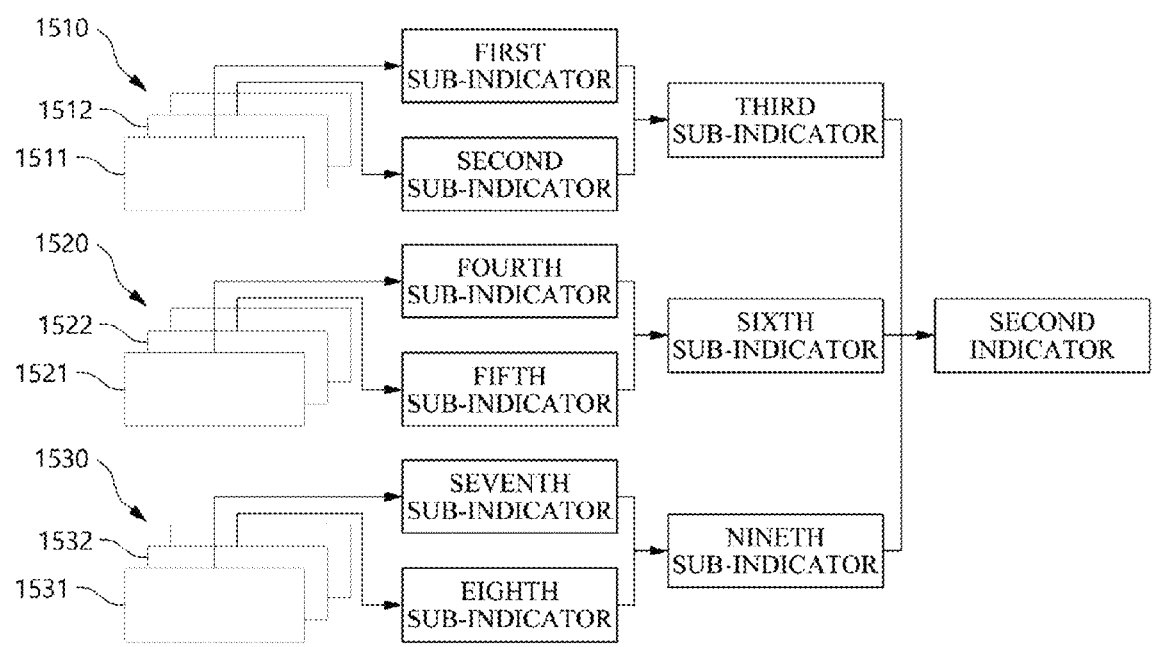
FIG. 15 is a diagram illustrating another embodiment for an electronic device for obtaining a second indicator based on a plurality of landmark images, according to various embodiments.

FIG. 15 is a diagram illustrating another embodiment for an electronic device to obtain a second indicator based on a plurality of landmark images, according to various embodiments.

Referring to FIG. 15, the electronic device may obtain a plurality of sub-indicators based on a plurality of landmark images, and it may obtain a second indicator associated with a second type of lesion based on the plurality of sub-indicators.

The electronic device may use a plurality of images corresponding to each landmark to accurately calculate a probability of a second type of lesion occurring for each landmark.

The electronic device may calculate the sub-indicator using a plurality of images corresponding to a landmark.

For example, the electronic device may obtain a sub-indicator associated with the second type of lesion based on the first landmark image group 1510 including the first image 1511 and the second image 1512 corresponding to the first landmark.

Specifically, the electronic device may obtain a first sub-indicator based on the first image 1511 corresponding to the first landmark and a second sub-indicator based on the second image 1512 corresponding to the first landmark. It may obtain a third sub-indicator representing the probability of a second type of lesion occurring in the first landmark based on the first and the second sub-indicator. In addition, the electronic device may obtain a fourth sub-indicator based on the third image 1521 included in the second landmark image group 1520 corresponding to the second landmark, obtain a fifth sub-indicator based on the fourth image 1522 corresponding to the second landmark, and obtain a third sub-indicator representing a probability of a second type of lesion occurring in the second landmark based on the fourth and the fifth sub-indicator. In addition, the electronic device may obtain a seventh sub-indicator based on a fifth image 1531 included in the third landmark image group 1530 corresponding to the third landmark, obtain an eighth sub-indicator based on a sixth image 1532 corresponding to the third landmark, and obtain a ninth sub-indicator representing a probability of a second type of lesion occurring in the third landmark based on the seventh sub-indicator and the eighth sub-indicator.

The electronic device may obtain a result value based on a plurality of sub-indicators to accurately calculate the probability of occurrence of a second type of lesion in a specific landmark. For example, the electronic device may obtain a third sub-indicator by selecting one of the first sub-indicator and the second sub-indicator. Alternatively, the electronic device may obtain the third sub-indicator based on the average of the first sub-indicator and the second sub-indicator.

Alternatively, the electronic device may verify the accuracy by calculating a plurality of sub-indicators based on a plurality of images corresponding to a landmark. The electronic device may consider the result as unreliable if the sub-indicators for each of the plurality of images corresponding to a landmark differ by more than a predetermined threshold. For example, the electronic device may recalculate the sub-indicator if the difference between the first sub-indicator and the second sub-indicator indicating the probability of occurrence of the second type of lesion in the first landmark exceeds a predetermined threshold. In this case, the electronic device may calculate the sub-indicator based on another image corresponding to the first landmark.

In addition, the electronic device may obtain a second indicator associated with the second type of lesion based on a plurality of sub-indicators for each of the plurality of landmarks.

Referring again to FIG. 13, the electronic device may obtain information about the second type of lesion including the second indicator. (s1330). The information about the second type of lesion may further include the second indicator and multiple sub-indicators indicating the probability of occurrence of the second type of lesion for each of the plurality of landmarks.

In addition, without being limited thereto, the electronic device may obtain information about the second type of lesion based on a plurality of image frames in the endoscopic image.

Figure 16:
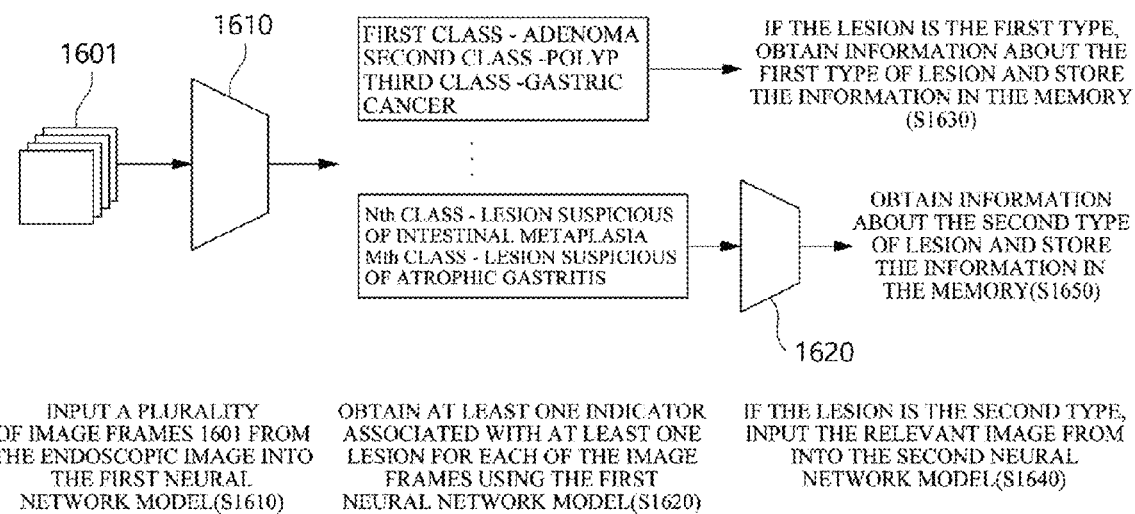
FIG. 16 is a diagram illustrating an embodiment in which an electronic device obtains information about a second type of lesion, according to various embodiments.

FIG. 16 is a diagram illustrating an embodiment in which an electronic device obtains information about a second type of lesion, according to various embodiments.

With reference to FIG. 16, the electronic device may input a plurality of image frames 1601 from the endoscopic image into the first neural network model (S1610). In this case, the first neural network model 1610 may be an artificial intelligence model trained to classify each of the plurality of image frames 1601 into one of several classes associated with the lesion.

The electronic device may obtain at least one indicator associated with at least one lesion for each of the image frames using the first neural network model 1610 (s1620). Specifically, the electronic device may classify each of the image frames as one of several classes corresponding to the plurality of lesions. The at least one indicator associated with the at least one lesion obtained by the electronic device may include a result value output by the first neural network model 1610.

If the lesion is the first type, the electronic device may obtain information about the first type of lesion and store the information in the memory (s1630). In this case, the first type of lesion may correspond to a plurality of predetermined classes. For example, the first type of lesion may include, but is not limited to, adenoma, polyp, or gastric cancer.

If the lesion is the second type, the electronic device may input the relevant image from into the second neural network model 1620 (s1640). In this case, the second neural network model 1620 may be a model trained to calculate the second indicator associated with the second type of lesion. That is, the electronic device may obtain the second indicator indicating the probability that corresponds to the second type of lesion using the second neural network model 1620. In this case, the second type of lesion may correspond to a plurality of predetermined classes. For example, the second type of lesion may include, but is not limited to, a lesion suspicious of intestinal metaplasia or a lesion suspicious of atrophic gastritis.

In addition, the electronic device may be configured to input a plurality of image frames corresponding to a plurality of predetermined landmarks into the second neural network model 1620. Accordingly, the electronic device may obtain the indicator associated with the second type of lesion based on the plurality of image frames corresponding to the plurality of landmarks.

The electronic device may obtain information about the second type of lesion and store the information in the memory (s1650). In this case, the information about the second type of lesion may indicate the probability of a specific image corresponding to the second type of lesion.

Referring again to FIG. 13, the electronic device may provide information about the second type of lesion using the display (s1340).

A method of providing information about the second type of lesion by the electronic device through a user interface will be described with reference to FIGS. 17 to 20.

[Method for Providing Information about a Lesion]

Figure 17:
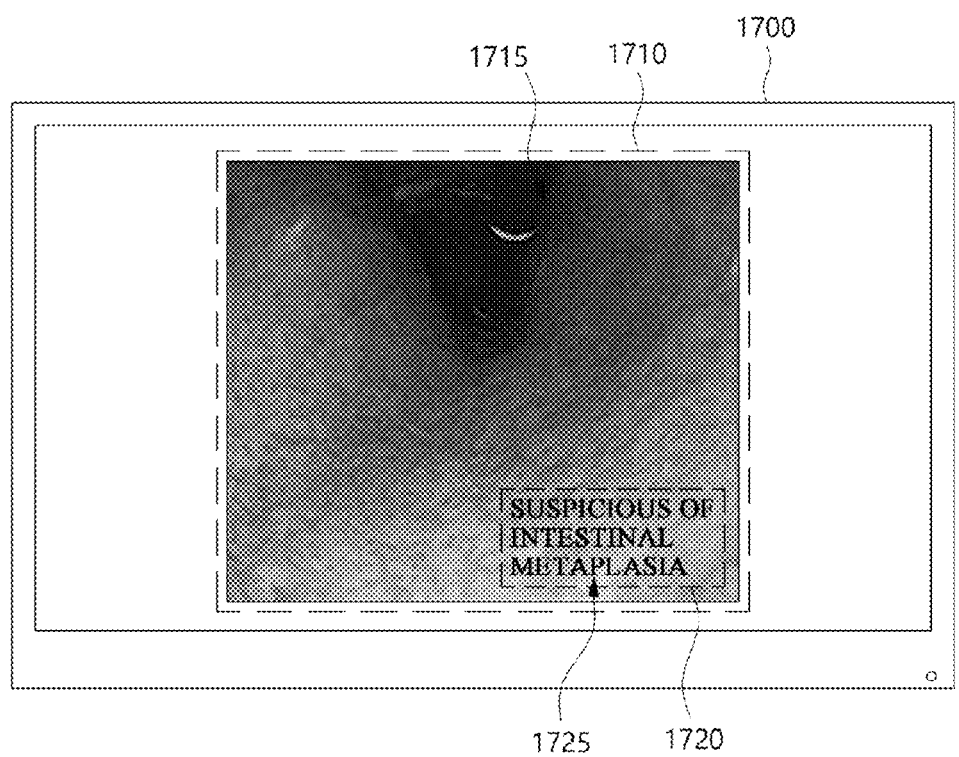
FIG. 17 is a diagram describing an example in which an electronic device provides information about a second type of lesion, according to various embodiments.

FIG. 17 is a diagram illustrating an example of the electronic device providing information about the second type of lesion according to various embodiments.

Figure 18:
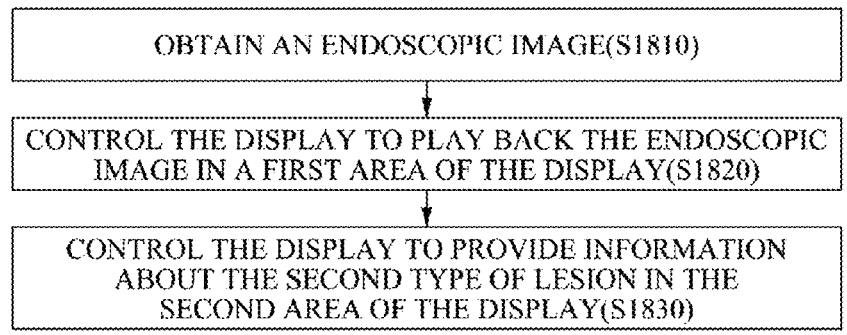
FIG. 18 is a flowchart illustrating a method of providing information about two types of lesions by an electronic device according to various embodiments.

FIG. 18 is a flowchart for describing a method of providing information about the second type of lesion by the electronic device according to various embodiments.

Referring to FIG. 18, the electronic device may obtain an endoscopic image from the endoscopic device (s1810). The electronic device may control the display to play back the endoscopic image in a first area of the display (s1820). In addition, the electronic device may control the display to provide information about the second type of lesion in the second area of the display (s1830).

In this case, the electronic device may provide information about the second type of lesion for an image frame. For example, the electronic device may provide information about the second type of lesion in real time during the endoscopic examination.

For example, referring to FIG. 17, the electronic device may provide information 1720 on the second type of lesion using the display 1700. The electronic device may control the display 1700 to play back the endoscopic image in the first area 1710 of the display 1700.

In addition, the electronic device may control the display 1700 to present a landmark image 1715 in the first area 1710 of the display. In this case, the landmark image 1715 is obtained based on the endoscopic image and may indicate a specific landmark inside the body. For example, the electronic device may provide the landmark image 1715 in the first area 1710 by pausing the playback of the endoscopic image when the image frame for the specific landmark is presented.

In addition, the electronic device may control the display 1700 to output the information 1720 about the second type of lesion in the second area 1720 of the display. In this case, the information 1720 about the second type of lesion may correspond to the image output in the first area 1710. Specifically, the information 1720 about the second type of lesion may indicate the possibility that the image output in the first area 1710 corresponds to the second type of lesion. For example, the second type of lesion information 1720 may include text, such as message indicating "suspicious for intestinal epithelialization," representing the probability of the occurrence of the second type of lesion.

That is, the electronic device may control the display 1700 to output the landmark image in the first area 1710 of the display and to output the information about the second type of lesion corresponding to the landmark image in the second area 1720 of the display.

In this case, the second area 1720 where the information about the second type of lesion is output may be a portion of the first area 1710. In addition, without being limited thereto, the second area 1720 where the information about the second type of lesion is output may be configured not to overlap with the first area 1710.

In addition, the location of the second area 1720 where the information about the second type of lesion is output may be adjusted based on user input.

Upon the occurrence of a predetermined event, the electronic device may activate the second area 1720 where the information about the second type of lesion is output. For example, when the electronic device identifies the image frame suspicious of the second type of lesion after playing back the endoscopic image, the electronic device may activate the second area 1720 to provide the information about the second type of lesion corresponding to the corresponding image frame.

In addition, the electronic device may provide the information about the second type of lesion for the plurality of image frames. In particular, the electronic device may provide the information about the second type of lesion corresponding to each of the plurality of landmark images, and it may provide comprehensive information about the second type of lesion based on the corresponding information. For example, the electronic device may provide the information about the second type of lesion by using an interface for the endoscopic examination result.

Figure 19:
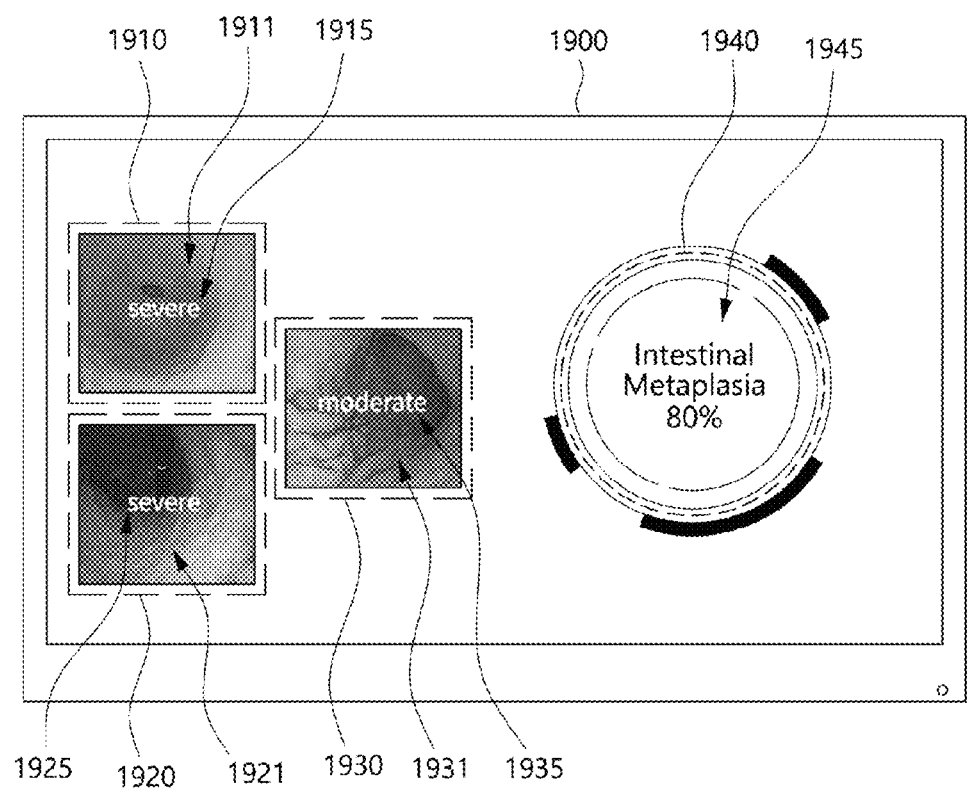
FIG. 19 is a diagram describing another example of an electronic device providing information about a second type of lesion, according to various embodiments.

FIG. 19 is a diagram illustrating another example where the electronic device provides information about the second type of lesion according to various embodiments.

Figure 20:
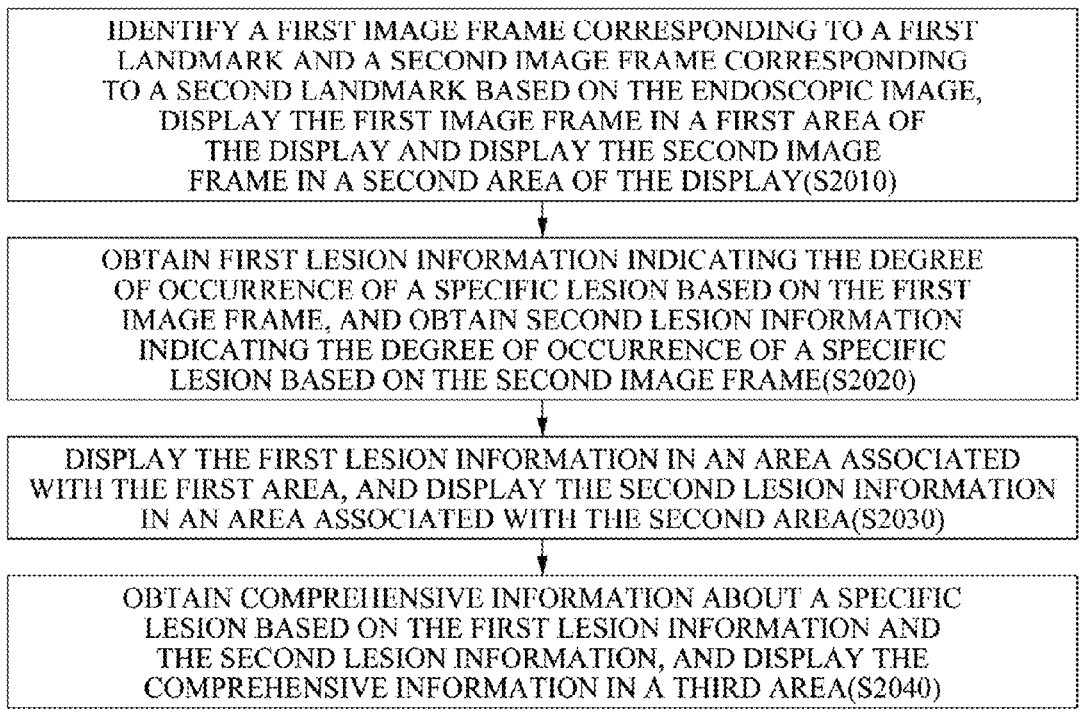
FIG. 20 is a flowchart illustrating a method of providing information about a second type of lesion by an electronic device, according to various embodiments.

FIG. 20 is a flowchart illustrating a method where the electronic device provides information about the second type of lesion according to various embodiments.

Referring to FIG. 20, the electronic device may identify a first image frame corresponding to a first landmark and a second image frame corresponding to a second landmark based on the endoscopic image. The electronic device may display the first image frame in a first area of the display and display the second image frame in a second area of the display (s2010). In this case, the second area may be configured not to overlap with the first area.

In addition, the electronic device may obtain first lesion information indicating the degree of occurrence of a specific lesion based on the first image frame, and it may obtain second lesion information indicating the degree of occurrence of a specific lesion based on the second image frame (s2020).

In addition, the electronic device may display the first lesion information in an area associated with the first area, and it may display the second lesion information in an area associated with the second area (s2030). Here, the area associated with the first area may be implemented in at least a portion of or adjacent to the first area. That is, the area associated with the first area may provide information corresponding to the image displayed in the first area.

In addition, the electronic device may obtain comprehensive information about a specific lesion based on the first lesion information and the second lesion information, and it may display the comprehensive information in a third area (s2040). The third area may be configured not to overlap with the first area and the second area.

With reference to FIG. 19, the electronic device may provide information about a specific lesion (e.g., intestinal epithelialization) via the display 1900. The electronic device may output a plurality of landmark images obtained at different times or locations during the endoscopic examination.

For example, the electronic device may output the first landmark image 1911 in the first area 1910 of the display. In addition, the electronic device may output the second landmark image 1921 in the second area 1920 of the display. The electronic device may output the third landmark image 1931 in the third area 1930 of the display. In this case, the first area 1910, the second area 1920, and the third area 1930 may be configured not to overlap each other.

In addition, the electronic device may provide information about a specific lesion corresponding to each of the plurality of landmark images using the display 1900.

Specifically, the electronic device may provide the first lesion information 1915 corresponding to the first landmark image 1911, the second lesion information 1925 corresponding to the second landmark image 1921, and the third lesion information 1935 corresponding to the third landmark image 1931 via the display 1900.

In this case, the electronic device may control the display 1900 to provide information about a specific lesion at a location associated with the area displaying the specific landmark image.

Specifically, the electronic device may provide information about a specific lesion at a location (e.g., adjacent area or at least a portion of the area) associated with the area where a specific landmark image is displayed.

For example, the electronic device may display the first lesion information 1915 (e.g., severe) in an area associated with the first area 1910, the second lesion information 1925 (e.g., severe) in an area associated with the second area 1920, and the third lesion information 1935 (e.g., moderate) in an area associated with the third area 1930.

In addition, the electronic device may provide comprehensive information 1945 about a specific lesion in the fourth area 1940 of the display 1900. In this case, the comprehensive information 1945 may include text (e.g., 80% of intestinal metaplasia) indicating the likelihood of a particular lesion (e.g., intestinal metaplasia).

In addition, the fourth area 1940 may be configured not to overlap with the first area 1910, the second area 1920, and the third area 1930.

Figure 21:
FIG. 21 is a diagram illustrating a method of providing information about a first type of lesion and information about a second type of lesion by an electronic device during an endoscopic examination according to various embodiments.

FIG. 21 is a diagram illustrating a method for an electronic device to provide information about a first type of lesion and information about a second type of lesion during an endoscopic examination according to various embodiments.

Referring to FIG. 21, the electronic device may obtain an endoscopic image and display the image in the first area of the display (s2110).

In addition, the electronic device may identify a first suspicious area corresponding to a first type of lesion based on the first image frame in the endoscopic image (s2120). At this time, the technical features of FIGS. 11 and 12 may be applied to the method for identifying the first suspicious lesion area by the electronic device.

In this case, the electronic device may stop playing back the endoscopic image, display the first image frame in the first area, and provide the first visual display at a location corresponding to the first suspicious area in the first area (s2130). The first visual display may be a visual effect for informing the user of the location and/or area of the first suspicious area in the first image frame.

In addition, the electronic device may play back the endoscopic image in the first area of the display (s2140).

In addition, the electronic device may obtain second lesion information related to the second type of lesion based on the second image frame in the endoscopic image (s2150). At this time, the technical features of FIGS. 13 to 16 may be applied to the method for obtaining second lesion information related to the second type of lesion by the electronic device. In addition, the second image frame may be a landmark image representing a specific landmark in the body.

In addition, the electronic device may stop playing back the endoscopic image, display the second image frame in the first area, and visually provide the information about the second lesion in the second area of the display (s2160).

[Lesion Examination Process Based on Operation Mode]

An electronic device according to an embodiment of the present disclosure may operate in at least one of a plurality of operation modes. Specifically, the electronic device may process the endoscopic image according to at least one operation mode to provide detection information of at least one lesion.

In this disclosure, the operation mode may be defined according to various factors related to the operation of at least one process. Specifically, the operation mode may be classified based on the type of data input to the at least one processor, the type of data output from the at least one processor, or the type of processor performing the operation.

For example, if different types of input are received by the at least one processor, the processor may operate in different modes. For example, the processor may operate in a first operation mode to process the endoscopic image when the endoscopic image is received, and it may operate in a second operation mode to process the landmark image when the landmark image is received.

As another example, when the output results differ in type, the at least one processor may operate in different modes of operation. Specifically, a plurality of operation modes may be set in a processor, and when one of the plurality of operation modes is operated, a predetermined form of result may be output. For example, the at least one processor may operate in at least one of a first mode of operation for outputting first detection information about a first type of lesion and a second mode of operation for outputting second detection information about a second type of lesion.

As another example, the mode of operation may be distinguished by a processor performing an operation. For example, a first processor for detecting the landmark image may be configured to operate in the first mode of operation, the second processor for detecting the first type of lesion may be configured to operate in the second mode of operation, and the third processor for detecting the second type of lesion may be configured to operate in the third mode of operation.

In addition, the modes of operation of the at least one processor may be configured to be switchable. In this case, the at least one processor may be configured to operate in only one mode at a time.

Furthermore, the at least one processor may be configured to operate in one or more operation modes at a particular time or simultaneously. In this case, the operation mode of the at least one processor may be implemented or terminated independently of each other.

In addition, the mode of operation of the at least one processor may be triggered by a predetermined event.

Figure 22:
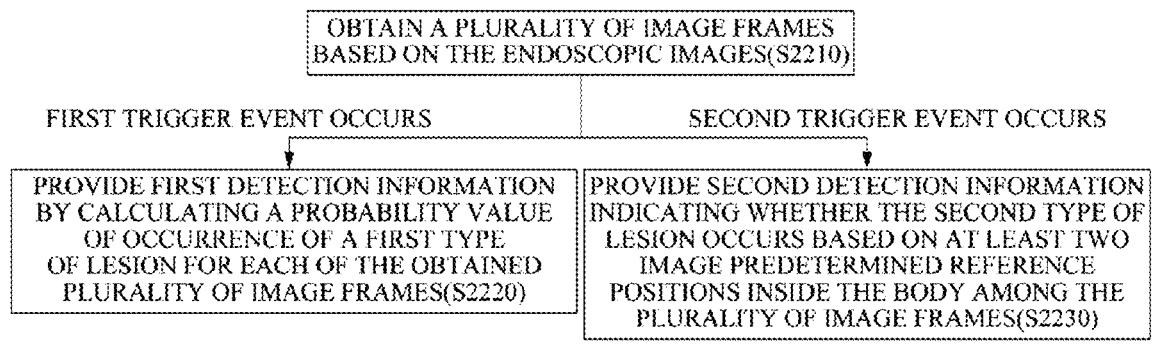
FIG. 22 is a flowchart illustrating a method of detecting a lesion according to at least one mode of operation by an electronic device according to various embodiments.

FIG. 22 is a flowchart illustrating a method for detecting a lesion by an electronic device according to at least one mode of operation according to various embodiments.

Figure 23:
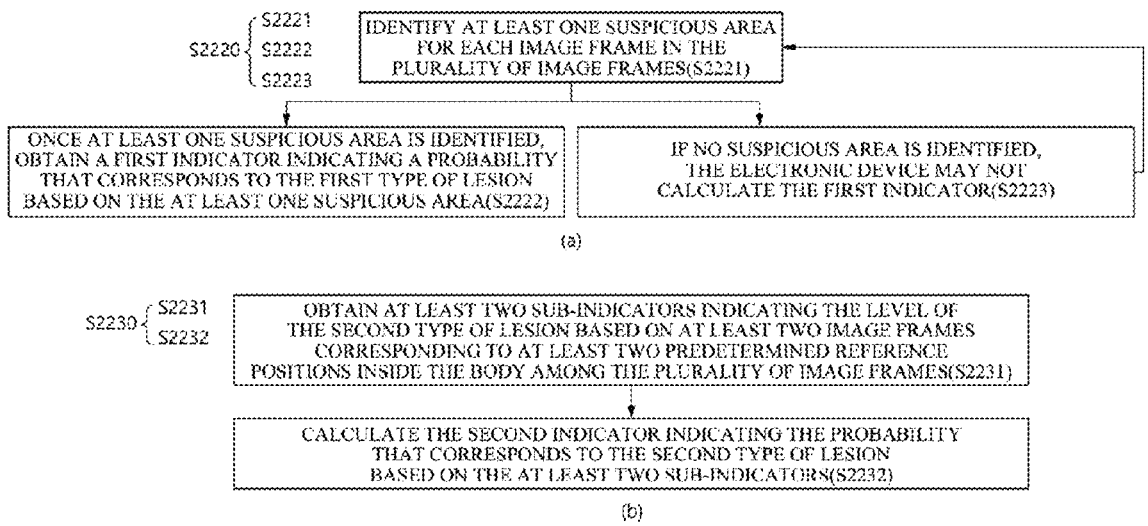
FIG. 23 is a flowchart illustrating a method of detecting a lesion according to at least one mode of operation by an electronic device according to various embodiments.

FIG. 23 is a flowchart illustrating another method for detecting a lesion by an electronic device according to at least one mode of operation, according to various embodiments.

With reference to FIG. 22, the electronic device may obtain a plurality of image frames based on the endoscopic images (s2210).

Upon the occurrence of the first trigger event, the electronic device may provide first detection information indicating whether the first type of lesion occurs based on at least one of the multiple image frames. Specifically, when a first trigger event occurs, the electronic device may enter a first mode of operation for detecting a first type of lesion. While the electronic device is operating in the first mode of operation, the electronic device may obtain information about the first type of lesion based on at least one of the multiple image frames.

For example, the electronic device may provide first detection information by calculating a probability value of occurrence of a first type of lesion for each of the obtained plurality of image frames (S2220). Alternatively, the electronic device may provide first detection information by calculating a probability value for the occurrence of a first type of lesion based on at least one image frame in which a suspicious lesion area is identified among the plurality of image frames.

For example, with reference to FIG. 23(a), the operation S2220 for obtaining first detection information may further include multiple operations while the electronic device is operating in the first mode of operation.

Specifically, the electronic device may identify at least one suspicious area for each image frame in the plurality of image frames (s2221). Here, the at least one suspicious area may correspond to a potential lesion in the image frame.

Once at least one suspicious area is identified, the electronic device may obtain a first indicator indicating a probability that corresponds to the first type of lesion based on the at least one suspicious area (s2222). In this case, the electronic device may provide first detection information including the first indicator indicating a probability that corresponds to the first type of lesion.

In addition, if no suspicious area is identified, the electronic device may not calculate the first indicator (s2223). The electronic device may perform the same operation (s2221) on the next image frame without calculating the result value corresponding to the image frame.

Referring to FIG. 22, the electronic device may provide second detection information indicating whether the second type of lesion occurs based on at least two image frames corresponding to at least two predetermined reference positions inside the body among the plurality of image frames, upon the occurrence of the second trigger event (s2230). In particular, when the second trigger event occurs, the electronic device may switch to the second mode of operation for detecting the second type of lesion. When the electronic device operates in the second mode of operation, the electronic device may obtain information about the second type of lesion based on at least two image frames corresponding to at least two predetermined reference positions among the plurality of image frames.

For example, the electronic device may identify at least two image frames corresponding to at least two predetermined landmark locations among the obtained plurality of image frames. In addition, the electronic device may obtain the second detection information by calculating the probability of corresponding to the second type of lesion based on the identified at least two image frames.

Referring to (b) of FIG. 23, for example, since the electronic device operates in the second mode of operation, the operation s2230 for obtaining the second detection information may further comprise a plurality of operations.

In particular, the electronic device may obtain at least two sub-indicators indicating the level of the second type of lesion based on at least two image frames corresponding to at least two predetermined reference positions inside the body among the plurality of image frames (s2231).

In addition, the electronic device may calculate the second indicator indicating the probability that corresponds to the second type of lesion based on the at least two sub-indicators (s2232). In this case, the electronic device may provide second detection information including the second indicator indicating the probability that corresponds to the second type of lesion.

Figure 24:
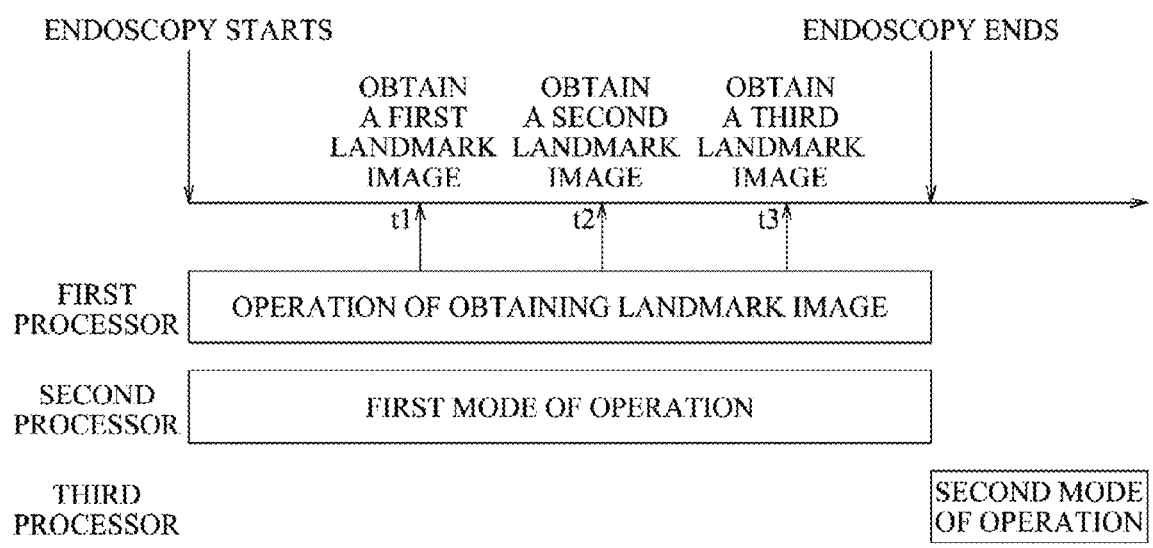
FIGS. 24, 25 and 26 are diagrams illustrating a time at which an electronic device performs at least two modes of operation according to various embodiments.
Figure 25:
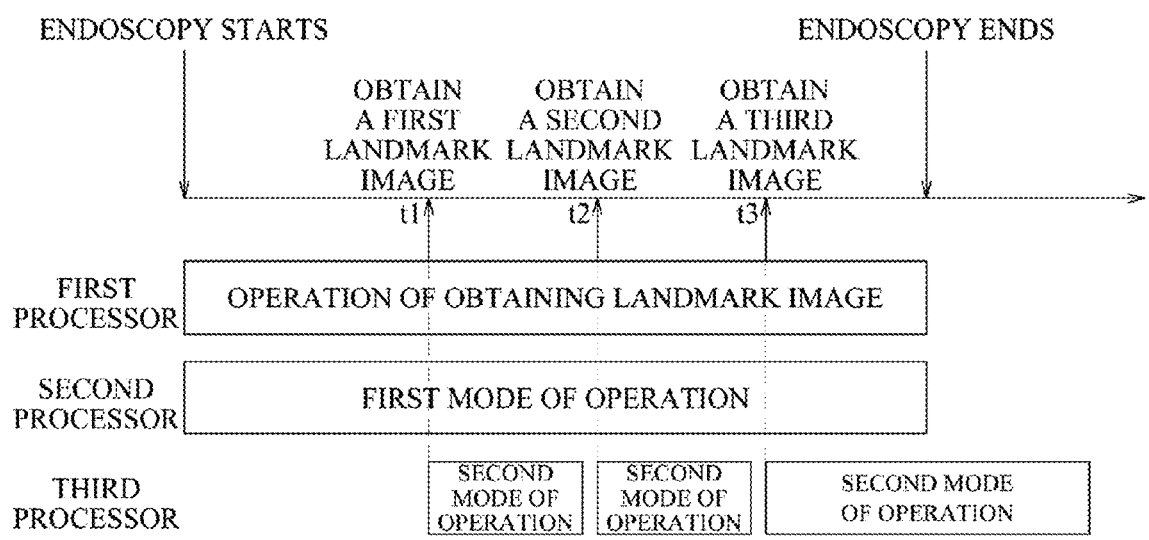
Figure 26:
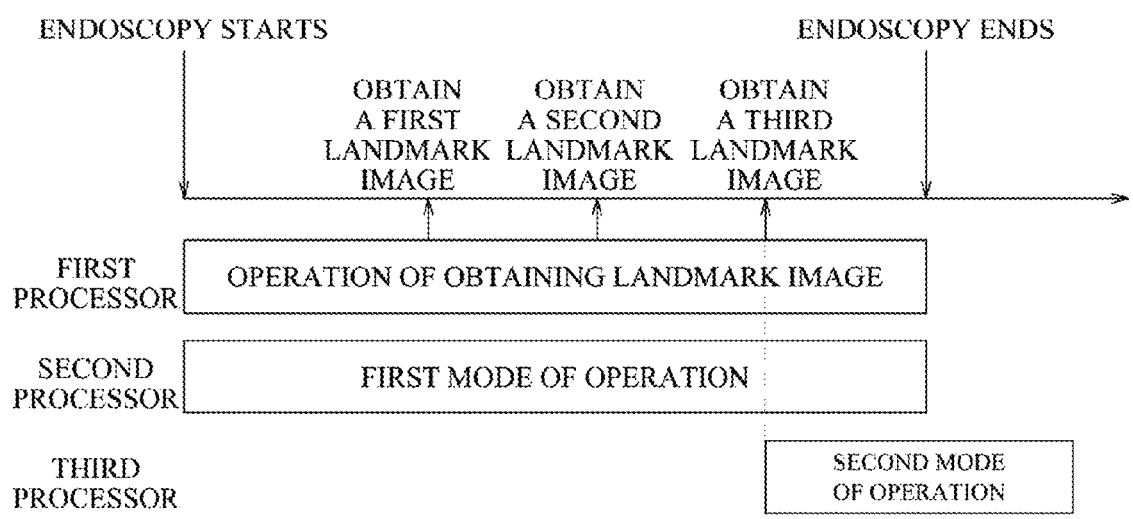

FIGS. 24 to 26 illustrate the timing of the enforcement of at least two modes of operations by the electronic device according to various embodiments.

In FIGS. 24 to 26, the operation of at least one processor (e.g., the first processor) for detecting a landmark image among the plurality of image frames is referred to as the "landmark image acquisition operation", the operation of at least one processor (e.g., the second processor) for obtaining detection information about the first type of lesion based on the plurality of image frames is referred to as the "first mode of operation." The operation of at least one processor (e.g., the third processor) for obtaining detection information about the second type of lesion based on the at least two landmark images is referred to as the "second mode of operation". While the first, second, and the third processors may be physically distinct processors, they are not limited as such and may represent that conceptual divisions of various functions implemented in a single processor.

The electronic device, according to one embodiment, may activate a predetermined mode of operation based on the occurrence of a predetermined trigger event. Such trigger event may include a start or end of a procedure (e.g., reception of an electrical signal requesting the start or end), an acquisition of a landmark image (e.g., a detection operation of the landmark image), or a user input indicating a specific operation.

The electronic device may terminate the operation mode when the information processing by the at least one processor is complete and the result value is output.

For example, referring to FIG. 24, when the endoscopy starts, the electronic device may perform the landmark image acquisition operation using the first processor, and it may implement the first mode of operation when the endoscopy starts using the second processor. The electronic device may detect the start of endoscopy based on the electrical signal received from the endoscopic device, and it may activate the landmark image acquisition operation and the first mode of operation by inputting the endoscopic image received from the endoscopic device to the first processor and the second processor, respectively.

The first processor may obtain the plurality of landmark images corresponding to the plurality of landmarks based on the received endoscopic image. In addition, the first processor may store information about the landmark image whenever the image corresponding to the at least one landmark is identified. For example, the first processor may obtain a first landmark image at the first time (t1), a second landmark image at the second time (t2), and a third landmark image at the third time (t3).

The second processor may obtain the first detection information about the first type of lesion based on the received endoscopic image. In this case, the first detection information may include result values indicating whether a first type of lesion corresponding to each of the plurality of image frames in the endoscopic image is detected.

Upon completion of the endoscopy, the electronic device may implement the second mode of operation using the third processor. The electronic device may detect the end of the endoscopic examination based on the electrical signal received from the endoscopic device and control the operation of the third processor accordingly.

The third processor may obtain the second detection information about the second type of lesion based on the at least two landmark images. For example, the third processor may obtain the information about the second type of lesion based on the first, second, third landmark images.

The electronic device may switch the mode of operation from the first mode of operation for identifying the first type of lesion to the second mode of operation for identifying the second type of lesion in response to the trigger event associated with the end of the endoscopic examination.

Additionally, the electronic device may perform the operation based on the user input indicating the specific operation.

For example, the electronic device may perform the operation of obtaining the landmark image based on the user input indicating the landmark image. In addition, the electronic device may implement the first mode of operation based on the user input indicating the first type of lesion. The electronic device may implement the second mode of operation based on user input indicating confirmation of the second type of lesion.

In another example, the electronic device may trigger the second mode of operation based on the acquisition of the landmark image.

Referring to FIG. 25, the electronic device may implement the second mode of operation via the third processor each time an image corresponding to a plurality of landmarks is obtained by the first processor.

In this regard, the electronic device may obtain second detection information for the second type of lesion by calculating a plurality of sub-indicators indicating the level of the second type of lesion for each of the plurality of landmark images.

When a trigger event associated with the acquisition of the landmark image occurs, the electronic device may calculate the plurality of sub-indicators by implementing the second mode of operation.

Specifically, the electronic device may obtain a first sub-indicator that corresponds to the first landmark image and is associated with the second type of lesion by implementing the second mode of operation at the first time t1 when the first landmark image is obtained. In addition, the electronic device may obtain the second sub-indicator that corresponds to the second landmark image and is associated with the second type of lesion by implementing the second mode of operation at the second time t2 when the second landmark image is obtained. In addition, the electronic device may obtain the third sub-indicator that corresponds to the third landmark image and is associated with the second type of lesion by implementing the second mode of operation at the third time t3 when the third landmark image is obtained.

In addition, the electronic device may obtain the second indicator indicating comprehensive information about the second type of lesion based on the plurality of sub-indicators.

In this case, when all the images corresponding to the predetermined number of landmarks are obtained, the electronic device may perform the second mode of operation to calculate the second indicator.

For example, when the third landmark image is obtained, the electronic device may calculate the third sub-indicator by implementing the second mode of operation. The electronic device may continuously calculate the second indicator without terminating the second mode of operation.

Alternatively, when the third landmark image is obtained, the electronic device may calculate the third sub-indicator by implementing the second mode of operation. Once the endoscopic examination is terminated after the second mode of operation, the electronic device may calculate the second indicator by re-implementing the second mode of operation.

In another example, the electronic device may be set to implement the second mode of operation when all of the predetermined number of landmark images are obtained.

Specifically, referring to FIG. 26, the electronic device may implement the second mode of operation using the third processor when all images corresponding to the predetermined number of landmarks are obtained by the first processor.

More specifically, the electronic device may implement the second mode of operation using the third processor when an image corresponding to three landmarks for detecting the second type of lesion is obtained.

For example, the electronic device may provide the second detection information about the second type of lesion by implementing the second mode of operation at the third time t3 when the third landmark image is obtained. Specifically, at the third time t3, the third processor may obtain the first sub-indicator based on the first landmark image, obtain the second sub-indicator based on the second landmark image, obtain the third sub-indicator based on the third landmark image, and obtain the second indicator associated with the second type of lesion by using the first, second, and the third sub-indicator.

Figure 27:
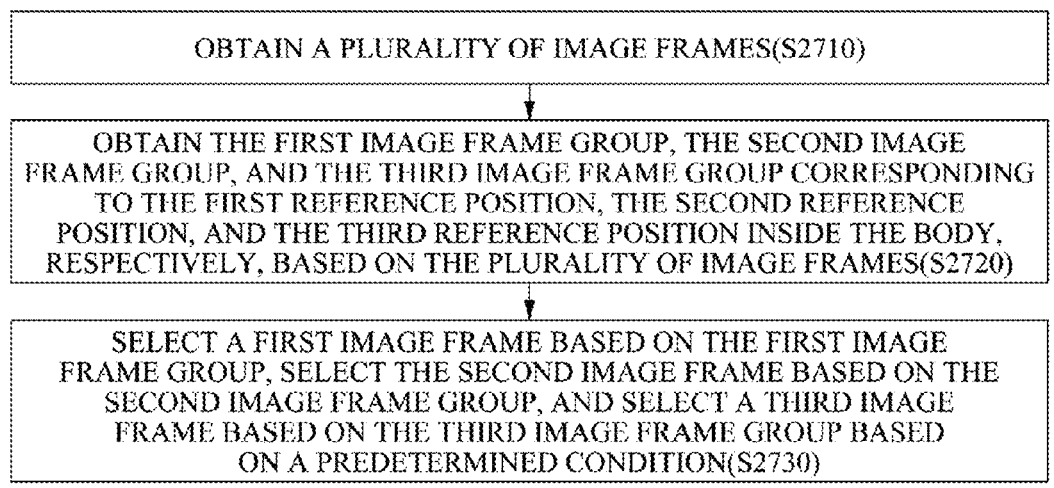
FIG. 27 is a flowchart illustrating a method of selecting a landmark image to obtain information about a second type of lesion by an electronic device according to various embodiments.

FIG. 27 is a flowchart illustrating a method of selecting a landmark image by an electronic device to obtain information about a second type of lesion, according to various embodiments.

An electronic device may obtain detection information about a second type of lesion (e.g., intestinal metaplasia) based on images corresponding to at least two landmarks. obtaining a high-quality landmark image is critical to ensuring an accurate result.

In order to obtain a high-quality landmark image, the electronic device can select the best image frame from among the plurality of image frames obtained for a landmark based on a predetermined condition.

For example, with reference to FIG. 27, the electronic device may obtain a plurality of image frames (s2710).

In addition, the electronic device may obtain the first image frame group, the second image frame group, and the third image frame group corresponding to the first reference position, the second reference position, and the third reference position inside the body, respectively, based on the plurality of image frames (s2720). In this case, the reference position may mean a location corresponding to the landmark.

The electronic device may select a first image frame based on the first image frame group, select the second image frame based on the second image frame group, and select a third image frame based on the third image frame group based on a predetermined condition (s2730).

The predetermined condition may be based on the quality of the image.

For example, the electronic device may select at least one image frame with high resolution from a plurality of landmark images. The electronic device may select an image frame closest to the center of the landmark from among the plurality of landmark images. In addition, the electronic device may select an image frame with the least portion covered by the endoscopic device or other internal body tissue among the plurality of landmark images.

In addition, the electronic device may obtain information about the second type of lesion based on the selected first, second, and the third image frames.

Without being limited thereto, the electronic device may provide the first image frame group, the second image frame group, and the third image frame group to the user for prompting the user to select an image to be used for analyzing the second type of lesion. In this case, the electronic device may obtain information about the second type of lesion by using at least one landmark image selected from the user.

Figure 28:
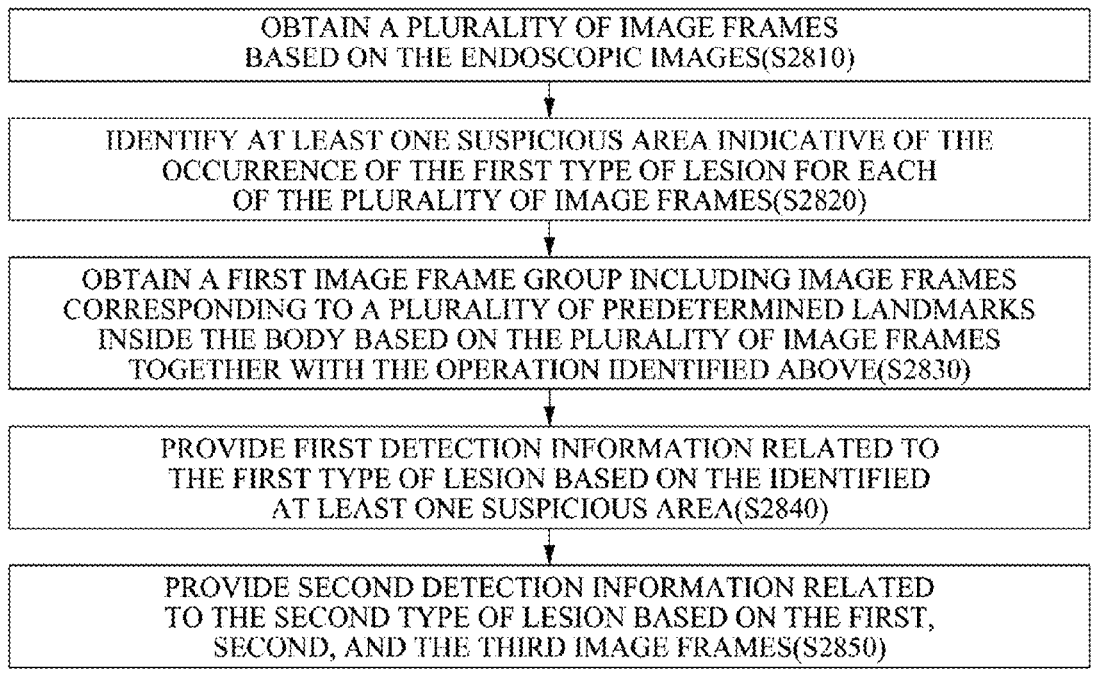
FIG. 28 is a flowchart illustrating a method of obtaining detection information about at least one lesion based on an endoscopic image by an electronic device according to various embodiments.

FIG. 28 is a flowchart illustrating a method for obtaining detection information for at least one lesion based on an endoscopic image by an electronic device according to various embodiments.

Referring to FIG. 28, the electronic device may obtain a plurality of image frames based on the endoscopic images (s2810).

The electronic device may identify at least one suspicious area indicative of the occurrence of the first type of lesion for each of the plurality of image frames (s2820).

The electronic device may obtain a first image frame group including image frames corresponding to a plurality of predetermined landmarks inside the body based on the plurality of image frames together with the operation identified above. (s2830). That is, the first image frame group here may include landmark images corresponding to predetermined landmarks.

In addition, the electronic device may provide first detection information related to the first type of lesion based on the identified at least one suspicious area (s2840).

Furthermore, the first image frame group may include a first image frame corresponding to the first landmark, a second image frame corresponding to the second landmark, and a third image frame corresponding to the third landmark. The electronic device may provide second detection information related to the second type of lesion based on the first, second, and the third image frames (s2850).

[User Interface for Providing Diagnosis Result]

The electronic device, according to an embodiment of the present disclosure, may provide detection information for at least one lesion by analyzing images obtained from the endoscopic device.

In this case, the electronic device may implement a user interface for providing detection information about the lesion, various examination results based on the detection information, and output the result through the display.

For example, the electronic device may guide the examiner to identify the endoscopic image for the main location by providing the images captured for each main landmark to the examiner.

Figure 29:
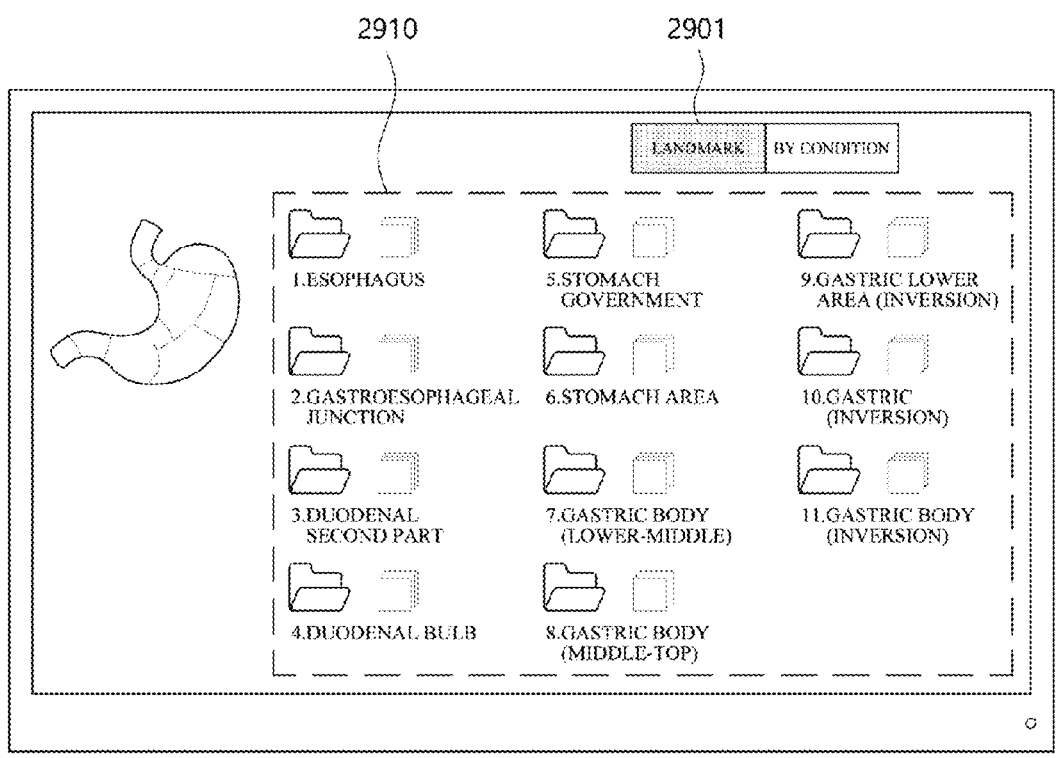
FIG. 29 is a diagram illustrating a user interface for providing image information for each landmark by an electronic device according to various embodiments.

FIG. 29 is a diagram illustrating a user interface for providing image information for each landmark by the electronic device according to various embodiments.

Referring to FIG. 29, the electronic device may provide image information 2910 for each landmark via the display.

Specifically, the electronic device may display the first icon 2901 implemented on the interface so that the user can identify the image corresponding to each landmark captured during the endoscopic examination. Upon receiving user input selecting the first icon 2901, the electronic device may display the image information 2910 for each landmark.

In this case, the electronic device may obtain the image information 2910 for each landmark by distinguishing and storing images corresponding to each of the plurality of predetermined landmarks for each landmark.

For example, the image information 2910 for each landmark may include a first set of images corresponding to the first landmark (e.g., the esophagus), a second set of images corresponding to the second landmark (e.g., the gastroesophageal junction), etc.

In addition, the electronic device may display at least one icon implemented on the interface so that the user can identify the images corresponding to the specific landmark. In particular, the electronic device may display a plurality of icons corresponding to each of the plurality of landmarks, and it may provide landmark images corresponding to the icon selected by the user among the plurality of icons via the display. In this case, the icon may be implemented as an icon in the form of a folder, but other forms are possible.

In another example, the electronic device may guide the examiner in identifying the image and the corresponding location for the major diseases by displaying the images in which the gastrointestinal disease is detected.

Figure 30:
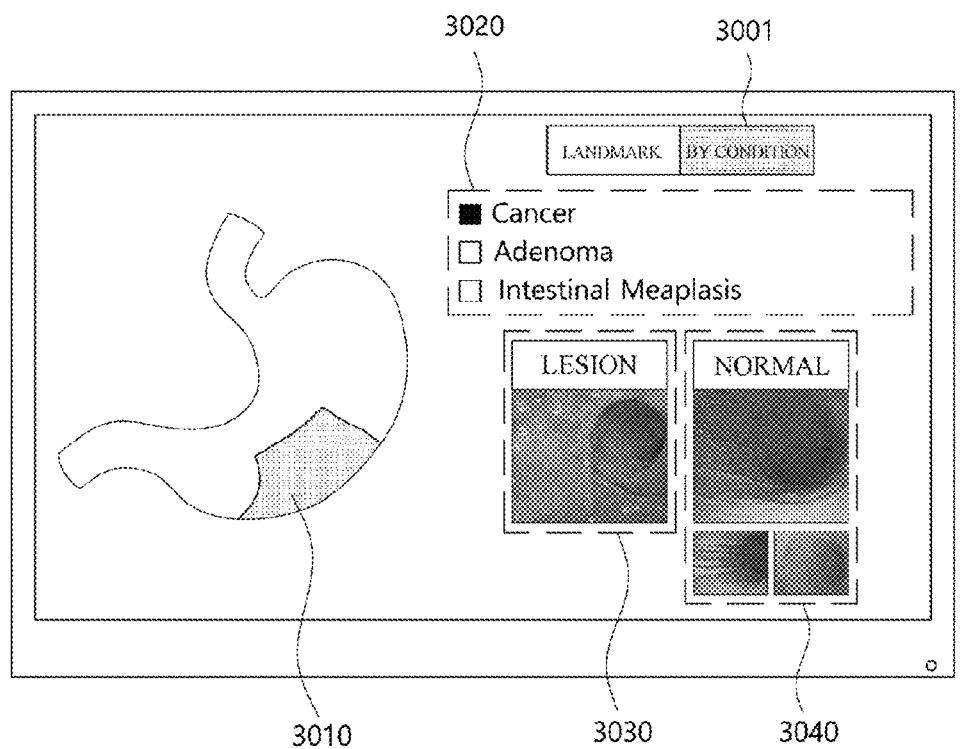
FIG. 30 is a diagram illustrating a user interface for providing image information for each disease by an electronic device according to various embodiments.

FIG. 30 is a diagram illustrating a user interface for providing image information for each disease by the electronic device according to various embodiments.

With reference to FIG. 30, the electronic device may provide image information for each disease via the display.

Specifically, the electronic device may display a second icon 3001 on the interface so that the user can identify the image and the corresponding location for each lesion (or gastrointestinal disease) when the endoscopic examination result is displayed. In addition, when a user input selecting the second icon 3001 is received, the disease information 3020, the image information 3030 and the location information 3010 may be displayed on the display.

The disease information 3020 may indicate a specific disease detected from a plurality of gastrointestinal diseases. For example, the electronic device may provide the disease information 3020 indicating at least one of cancer, adenoma, and intestinal metaplasia in connection with the detected lesion. The diseases shown in FIG. 30 are exemplary, and it is understood that gastrointestinal diseases generally known in medicine may be further included throughout the present disclosure.

In addition, the image information 3030 may indicate an image where a lesion corresponding to the disease information 3020 is detected during the endoscopic examination. each image identified by the image information 3030 may correspond to one of the predetermined landmarks.

In addition, the location information 3010 may indicate the approximate location where a gastrointestinal disease is detected. In addition, the location information 3010 may indicate a location where an image identified by the image information 3030 is captured.

Specifically, the electronic device may indicate a location where a gastrointestinal disease is detected or an image related to the landmark is obtained among a plurality of landmark locations.

For example, the electronic device may display a plurality of areas allocated to each of the plurality of landmarks. In addition, the electronic device may highlight an area associated with the location where the disease-detected image was captured.

Alternatively, upon receiving a user input selecting a specific area from the plurality of areas, the electronic device may provide the disease information and the image information corresponding to the selected area via the display.

In addition, the electronic device may further provide the comparison image information 3040 to compare the specific area. The comparison image information 3040 may indicate an image obtained at the same location as the image where a lesion is detected. That is, the comparison image information 3040 may indicate an image prestored in the memory of the electronic device rather than the image obtained during the endoscopic examination where the image information 3030 is obtained.

As another example, the electronic device may automatically generate a report of the endoscopic examination results, providing the user with detailed information regarding the examination and its findings.

FIG. 31 is a diagram illustrating a user interface of the electronic device for providing a report of the endoscopic examination result according to various embodiments.

Referring to FIG. 31, the electronic device may automatically generate and provide the examination report 3100 including various details related to the endoscopic examination on the display.

The examination report 3100 may include patient information 3110 regarding an individual being examined, examination image information 3120 including at least one image data obtained during the examination, comment information 3130 entered by the examiner, diagnosis information 3140 based on the endoscopic examination result, and additional information 3150.

In particular, the electronic device may obtain the examination image information 3120 based on at least one image in which at least one lesion is detected during the endoscopic examination.

The electronic device may obtain the comment information 3130 based on a comment on the endoscopic examination results provided by the examiner.

The electronic device may obtain the diagnosis information 3140 based on at least one lesion (or disease) suspicious of the endoscopic examination result.

In addition, the additional information 3150 may include a QR code for accessing a preventive management platform for the patient.

The electronic device may provide the examination information for each patient who has undergone an endoscopic examination. Specifically, the user (e.g., a doctor) may store the endoscopic examination results and review them using a graphical user interface (GUI) provided by the electronic device.

In this case, the electronic device may store the endoscopic images (e.g., existing data stored in PACS) for each patient by classifying them into a plurality of landmarks using the landmark classification function. Accordingly, the electronic device can provide the user with the endoscopic images classified by landmark and examination date.

According to the landmark automatic classification function of the electronic device, the user may use the pre-existing endoscopic image data stored in the hospital's medical image storage and transmission system (PACS) to provide the examination information for each patient. That is, the electronic device enables a systematic classification system by utilizing the endoscopic image previously stored in the existing system as well as the endoscopic image newly processed by the electronic device, generating the endoscopic result.

The user may use this examination information for medical consultation or to compare patient data for each treatment periods.

Figure 32:
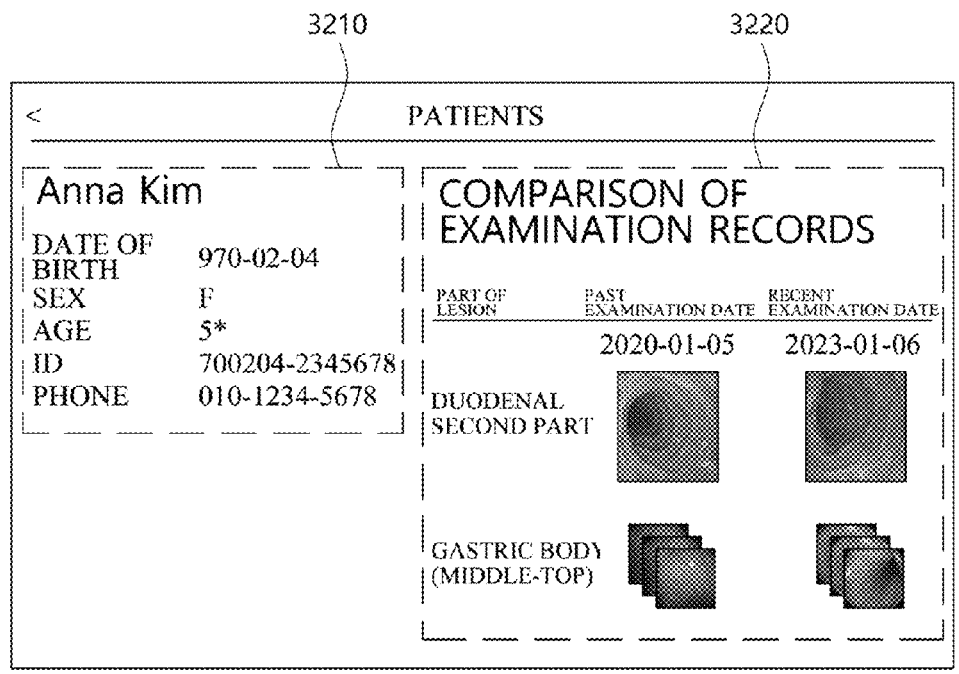
FIG. 32 is a diagram illustrating an example of a user interface for providing a result of diagnosis of a patient by an electronic device according to various embodiments.

FIG. 32 is a diagram illustrating an example of a user interface for the electronic device to provide the result of the examination information for each patient according to various embodiments.

Referring to FIG. 32, the electronic device may provide the user interface including the patient information 3210 and the examination information 3220 on the display.

Specifically, the electronic device may provide the patient information 3210 indicating the patient's physical information to be endoscopically examined and the examination information 3220 about the endoscopic examination result of the patient to provide the user interface indicating the information about the endoscopic examination result for each patient.

In this case, the examination information 3220 may include information about the endoscopic examination result performed over multiple days. Specifically, the electronic device may obtain the examination information 3220 including the endoscopic image obtained in the endoscopic examination performed on the previous day and the endoscopic image obtained in the endoscopic examination performed on the recent day.

In addition, the examination information 3220 may include information about the endoscopic examination result corresponding to each landmark. Specifically, the electronic device may classify the plurality of images in the endoscopic examination performed in the past and the endoscopic examination performed recently as the plurality of landmarks and obtain the examination information 3220 including the plurality of images classified into the plurality of landmarks.

In addition, without being limited thereto, the electronic device may obtain the diagnosis information 3220 by displaying comparisons of endoscopic image captured at the same location across different days of examination, especially at locations where specific diseases were previously detected.

A detailed method of generating the diagnosis information 3220 by the electronic device based on the endoscopic images will be described with reference to FIG. 33.

Figure 33:
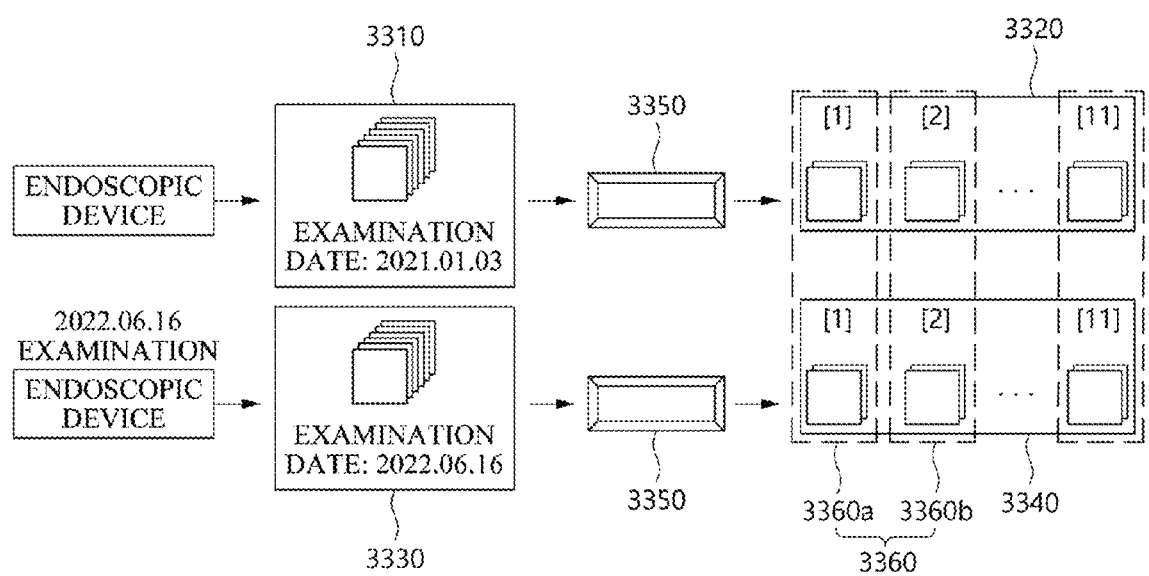
FIG. 33 is a diagram illustrating a method of automatically classifying and storing image information for each landmark based on an endoscopic image already stored by an electronic device according to various embodiments.

FIG. 33 is a diagram describing a method in which the electronic device automatically classifies and stores image information for each landmark based on the pre-stored endoscopic images, according to various embodiments.

Referring to FIG. 33, the electronic device may classify and store the endoscopic image obtained from the endoscopic device into multiple landmarks by processing the endoscopic image in a predetermined manner.

The electronic device may obtain the first classification information 3320 based on the first image information 3310 obtained from the endoscopic device and stored in the memory. In this case, the first image information 3310 may include the endoscopic image captured during an endoscopic examination conducted on the first day of diagnosis date, and such information may be stored in the PACS system. The first image information 3310 may include the examination date of diagnosis and associated endoscopic image data according to the endoscopic diagnosis performed on the corresponding date.

In addition, the electronic device may obtain the first classification information 3320 by inputting the first image information 3310 to the landmark classification model 3350.

In this case, the first classification information 3320 may be information stored in a form in which at least a portion of the plurality of image frames in the first image information 3310 is classified into one of the plurality of landmarks. Specifically, the first classification information 3320 may include at least one image corresponding to the first landmark and at least one image corresponding to the second landmark, and it may include at least one image corresponding to each of a plurality (e.g., 11) of landmarks.

In order to classify the image using the landmark classification model 3350, the electronic device may employ a landmark detection algorithm on the at least one image frame form the stored endoscopic images, enabling automatic classification and storage based on detected landmarks. That is, the electronic device may perform the automatic landmark classification using the detection algorithm based on the plurality of image frames in the prestored endoscopic image.

In addition, the electronic device may obtain the second classification information 3340 based on the second image information 3330 obtained from the endoscopic device. In this case, the second image information 3330 may include the endoscopic image obtained as the diagnosis performed on the second day of the diagnosis. That is, the second image information 3330 may include real-time endoscopic image obtained from the endoscopic diagnosis and may be data pre-stored in the PACS system.

The technical means related to the second classification information 3340 are the same as the technical means related to the first classification information 3320 described above, and therefore a detailed description is omitted.

The electronic device may provide the landmark information 3360 generated while the image information is being classified. In this case, the landmark information may include the endoscopic image information corresponding to the specific landmark and the date of diagnosis obtained from the endoscopic image. The electronic device may provide the multiple landmark information to compare the image obtained from the past diagnosis and the image obtained according from the recent diagnosis for each landmark. For example, the electronic device may include first landmark information 3360a including the time-specific endoscopic image corresponding to the first landmark and second landmark information 3360b including the time-specific endoscopic image corresponding to the second landmark. The electronic device may provide the time-specific endoscopic image corresponding to each of the plurality of landmarks as part of the landmark information.

Figure 34:
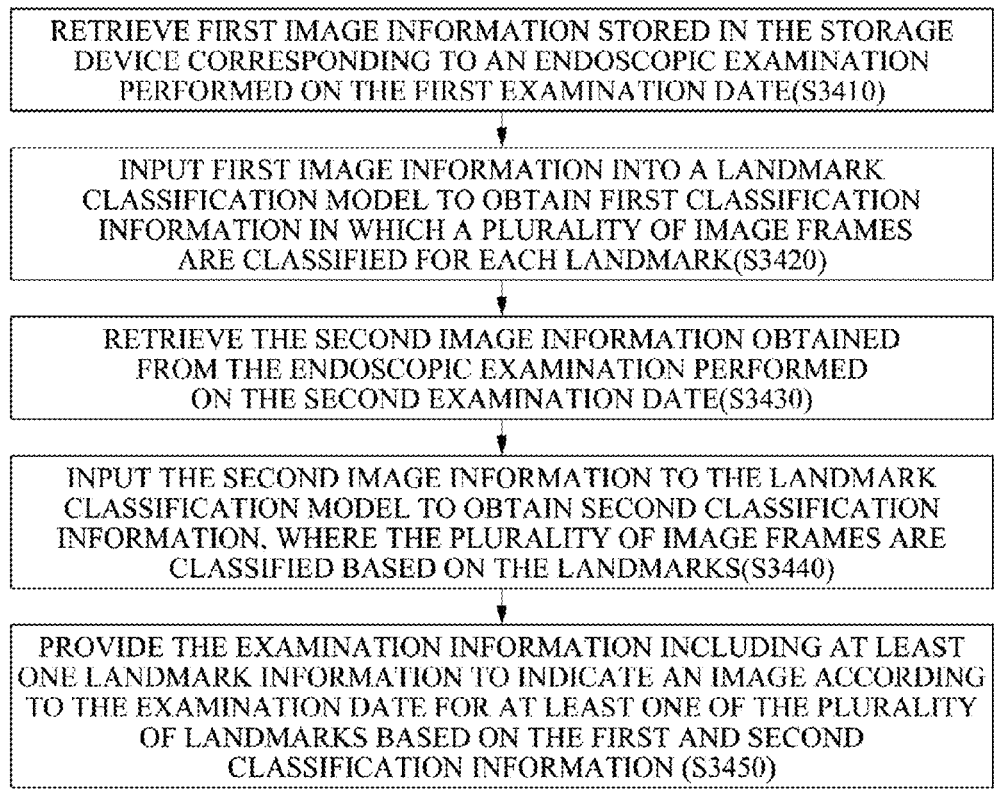
FIG. 34 is a flowchart illustrating a method of providing diagnostic information for each patient according to time by an electronic device according to various embodiments.

FIG. 34 is a flowchart illustrating a method for an electronic device to provide time-specific examination information for each patient according to various embodiments.

Referring to FIG. 34, the electronic device may retrieve first image information stored in the storage device corresponding to an endoscopic examination performed on the first examination date (s3410). The electronic device may input first image information into a landmark classification model to obtain first classification information in which a plurality of image frames are classified for each landmark (s3420). In addition, the electronic device may retrieve the second image information obtained from the endoscopic examination performed on the second examination date (s3430). The electronic device may input the second image information to the landmark classification model to obtain second classification information, where the plurality of image frames are classified based on the landmarks. (s3440). In addition, the electronic device may provide the examination information including at least one landmark information to indicate an image according to the examination date for at least one of the plurality of landmarks based on the first and second classification information. (s3450).

As described, although embodiments have been shown and described with reference to specific examples, it should be understood that various changes and modifications can be made by those skilled in the art without departing from the scope of the claims. For example, the described methods may be performed in a different order, and the described systems, structures, devices, or circuits may be combined or rearranged in different ways, replaced with equivalents, or substituted by other elements while still achieving the desired results.

Therefore, other implementations, modifications, and equivalents thereto will be within the scope of the claims described below.

The invention claimed is:

1. An electronic device for processing an endoscopic image, the device comprising:
   a memory configured to store instructions; and
   at least one processor electronically connected to the memory and configured to execute at least a portion of the instructions,
   wherein the at least one processor is configured to:
      obtain an indicator associated with at least one lesion by operating in at least one of a plurality of operation modes;
      obtain a plurality of image frames from the endoscopic image;
      obtain, in a first mode of operation, first detection information about a first type of lesion based on at least one of the plurality of image frames;
      determine at least two image frames corresponding to each of at least two predetermined reference positions among a plurality of reference positions inside a body based on the plurality of image frames; and
      obtain, in a second mode of operation, second detection information about a second type of lesion based on the at least two image frames.

2. The electronic device of claim 1, wherein the first detection information includes a first indicator indicating probability that corresponds to a first type of lesion, and wherein the at least one processor obtains the first indicator based on at least one suspicious lesion area if the at least one suspicious lesion area is identified in an image frame among the plurality of image frames.

3. The electronic device of claim 2, wherein the at least one processor is configured to refrain from obtaining a first indicator indicating the probability of a first type of lesion for at least one image frame in which no suspicious lesion area is identified among the plurality of image frames.

4. The electronic device of claim 1, wherein the at least one processor is configured to obtain at least two image frames corresponding to each of at least two predetermined reference positions inside the body from the plurality of image frames according to a landmark image acquisition operation.

5. The electronic device of claim 4, wherein the at least one processor is configured to calculate probability of corresponding to each of a plurality of predetermined reference positions based on each of the plurality of image frames according to the landmark image acquisition operation.

6. The electronic device of claim 1, wherein the at least two image frames include a first image frame corresponding to a first reference position and a second image frame corresponding to a second reference position, and wherein the at least one processor is configured to:
- obtain a first sub-indicator indicating a degree of the second type of lesion at the first reference position based on the first image frame;
- obtain a second sub-indicator indicating a degree of the second type of lesion at the second reference position based on the second image frame; and
- obtain the second detection information based on the first sub-indicator and the second sub-indicator.

7. The electronic device of claim 1, wherein the at least one processor includes a first processor and a second processor, wherein the first processor operates in the first mode of operation, and the second processor operates in the second mode of operation.

8. The electronic device of claim 1, wherein the at least one processor is configured to operate in the first mode of operation in response to a first trigger event and operate in the second mode of operation in response to a second trigger event.

9. The electronic device of claim 1, wherein the first mode of operation is implemented at a time when an endoscopic examination begins and is switched from the first mode of operation to the second mode of operation when the endoscopic examination ends.

10. The electronic device of claim 1, wherein the second mode of operation is implemented each time the at least two image frames are identified.

11. The electronic device of claim 1, wherein the second mode of operation is implemented when all of the at least two image frames are identified.

12. The electronic device of claim 1, wherein the at least one processor is configured to generate a result report for the endoscopic examination based on the first detection information and the second detection information.

13. The electronic device of claim 1, wherein the first type of lesion includes at least one of early gastric cancer, advanced gastric cancer, adenoma or polyps, and the second type of lesion includes at least one of intestinal metaplasia or atrophic gastritis.

14. A method of operating an electronic device for processing an endoscopic image, the method comprising:
- obtaining a plurality of image frames included in the endoscopic image using at least one processor in the electronic device;
- obtaining first detection information for a first type of lesion based on at least one of the plurality of image frames in a first mode of operation;
- determining at least two image frames corresponding to each of at least two predetermined reference positions among a plurality of reference positions inside a body based on the plurality of image frames; and
- obtaining second detection information for a second type of lesion based on the at least two image frames in a second mode of operation.

15. An endoscopic examination system, comprising:
an endoscopic device configured to capture an endoscopic image; and
at least one processor,
wherein the at least one processor is configured to:
- obtain a plurality of image frames included in the endoscopic image;
- obtain first detection information for a first type of lesion based on at least one of the plurality of image frames in a first mode of operation
- determine at least two image frames corresponding to each of at least two predetermined reference positions among a plurality of reference positions inside a body based on the plurality of image frames; and
- obtain second detection information for a second type of lesion based on the at least two image frames in a second mode of operation.

* * * * *